(12) United States Patent
Rome et al.

(10) Patent No.: US 10,933,018 B2
(45) Date of Patent: Mar. 2, 2021

(54) ISOTRETINOIN FORMULATIONS AND USES AND METHODS THEREOF

(71) Applicant: TIMBER PHARMACEUTICALS LLC, Woodcliff Lake, NJ (US)

(72) Inventors: Zachary Rome, Nyack, NY (US); Charles Rodney Greenaway Evans, Worthing (GB); Marc Barry Brown, Herts (GB); Francesco Caserta, Aldershot (GB)

(73) Assignee: Timber Pharmaceuticals LLC, Woodcliff Lake, NJ (US)

( * ) Notice: Subject to any disclaimer, the term of this patent is extended or adjusted under 35 U.S.C. 154(b) by 0 days.

(21) Appl. No.: 15/772,456

(22) PCT Filed: Oct. 26, 2016

(86) PCT No.: PCT/US2016/058746
§ 371 (c)(1),
(2) Date: Apr. 30, 2018

(87) PCT Pub. No.: WO2017/074982
PCT Pub. Date: May 4, 2017

(65) Prior Publication Data
US 2018/0318245 A1    Nov. 8, 2018

Related U.S. Application Data

(60) Provisional application No. 62/301,759, filed on Mar. 1, 2016, provisional application No. 62/248,760, filed on Oct. 30, 2015.

(51) Int. Cl.
| | | |
|---|---|---|
| *A61K 9/06* | (2006.01) | |
| *A61P 17/04* | (2006.01) | |
| *A61K 47/10* | (2017.01) | |
| *A61K 47/14* | (2017.01) | |
| *A61K 31/203* | (2006.01) | |
| *A61Q 19/00* | (2006.01) | |
| *A61K 45/06* | (2006.01) | |
| *A61K 31/198* | (2006.01) | |

(52) U.S. Cl.
CPC .............. *A61K 9/06* (2013.01); *A61K 31/198* (2013.01); *A61K 31/203* (2013.01); *A61K 45/06* (2013.01); *A61K 47/10* (2013.01); *A61Q 19/00* (2013.01)

(58) Field of Classification Search
CPC .......... A61K 9/06; A61K 47/10; A61K 47/14; A61K 31/198; A61K 31/203; A61K 45/06; A61P 17/04; A61Q 19/00
See application file for complete search history.

(56) References Cited

U.S. PATENT DOCUMENTS

| | | |
|---|---|---|
| 5,051,449 A | 9/1991 | Kligman |
| 5,158,773 A | 10/1992 | Gross |
| 5,252,604 A | 10/1993 | Nagy et al. |
| 5,420,147 A | 5/1995 | Van Wauwe et al. |
| 5,652,228 A | 7/1997 | Bissett |
| 5,721,275 A | 2/1998 | Bazzano |
| 5,834,513 A | 11/1998 | Ptchelintsev et al. |
| 6,051,609 A | 4/2000 | Yu et al. |
| 6,069,169 A | 5/2000 | Ptchelintsev et al. |
| 6,093,706 A | 7/2000 | Zeligs |
| 6,551,605 B2 | 4/2003 | Bonds |
| 6,599,513 B2 | 7/2003 | Deckers et al. |
| 6,740,327 B2 | 5/2004 | Yu et al. |
| 6,759,396 B1 | 7/2004 | Michel et al. |
| 7,083,799 B1 | 8/2006 | Giacomoni |
| 7,682,623 B2 | 3/2010 | Eini et al. |
| RE41,339 E | 5/2010 | Yu et al. |
| 8,466,128 B2 | 6/2013 | Lewis |
| 8,486,374 B2 * | 7/2013 | Tamarkin ............. A61K 9/0014 424/45 |
| 8,697,098 B2 | 4/2014 | Perumal et al. |
| 8,795,693 B2 | 8/2014 | Tamarkin et al. |
| 8,865,694 B2 | 10/2014 | Purcell |
| 8,900,553 B2 | 12/2014 | Tamarkin et al. |
| 9,072,667 B2 | 7/2015 | Tamarkin et al. |
| 9,167,813 B2 | 10/2015 | Tamarkin et al. |
| 9,265,726 B2 | 2/2016 | Abram et al. |
| 9,375,477 B2 | 6/2016 | Duprat |
| 2003/0017130 A1 | 1/2003 | Yu et al. |
| 2004/0214215 A1 | 10/2004 | Yu et al. |
| 2005/0014729 A1 | 1/2005 | Pulaski |
| 2005/0031547 A1 | 2/2005 | Tamarkin et al. |

(Continued)

FOREIGN PATENT DOCUMENTS

| | | |
|---|---|---|
| EP | 0365519 B1 | 3/1993 |
| WO | WO 93/10754 A1 | 6/1993 |

(Continued)

OTHER PUBLICATIONS

Tashtoush et al (International Journal of Pharmaceutics, 2008; 352(1-2):123-128). (Year: 2008).*

(Continued)

*Primary Examiner* — Marcos L Sznaidman
*Assistant Examiner* — Rayna Rodriguez
(74) *Attorney, Agent, or Firm* — Duane Morris LLP

(57) ABSTRACT

Provided herein are novel isotretinoin formulations that provide an enhanced targeted dermal delivery system for the drug isotretinoin with improved thermodynamic activity using no to a small level of ethanol relative to existing isotretinoin gel products, and methods for treatment of ichthyosis and other skin conditions using the same.

12 Claims, 16 Drawing Sheets

(56) References Cited

U.S. PATENT DOCUMENTS

| | | |
|---|---|---|
| 2005/0159485 A1 | 7/2005 | Jost-Price et al. |
| 2005/0186147 A1 | 8/2005 | Tamarkin et al. |
| 2005/0214328 A1 | 9/2005 | Zeldis |
| 2006/0177392 A1 | 8/2006 | Walden |
| 2007/0292355 A1 | 12/2007 | Tamarkin et al. |
| 2007/0292461 A1 | 12/2007 | Tamarkin et al. |
| 2008/0207570 A1 | 8/2008 | Segura-Orsoni |
| 2009/0004232 A1 | 1/2009 | Brzokewicz |
| 2009/0053290 A1 | 2/2009 | Sand et al. |
| 2009/0214628 A1 | 8/2009 | de Rijk |
| 2012/0087872 A1 | 4/2012 | Tamarkin et al. |
| 2012/0164087 A1 | 6/2012 | Carter |
| 2012/0259014 A1 | 10/2012 | Motwani et al. |
| 2013/0108557 A1 | 5/2013 | Abram et al. |
| 2013/0251644 A1 | 9/2013 | Majhi et al. |
| 2014/0249490 A1 | 9/2014 | Friedman et al. |
| 2015/0125520 A1 | 5/2015 | Mallard |
| 2015/0147403 A1 | 5/2015 | Djedour |
| 2015/0164907 A1 | 6/2015 | Oehlen et al. |
| 2015/0190372 A1 | 7/2015 | Djedour |
| 2016/0128944 A1 | 5/2016 | Chawrai et al. |

FOREIGN PATENT DOCUMENTS

| | | | | |
|---|---|---|---|---|
| WO | WO 2005/018530 A2 | 3/2005 | | |
| WO | WO-2010134047 A2 * | 11/2010 | ........... | A61K 9/0095 |
| WO | WO-2012053013 A2 * | 4/2012 | ........... | A61K 9/0014 |
| WO | WO 2013/106643 A2 | 7/2013 | | |
| WO | WO 2013/138744 A1 | 9/2013 | | |
| WO | WO 2013/170147 A1 | 11/2013 | | |
| WO | WO 2014/049295 A1 | 4/2014 | | |
| WO | WO 2014/049296 A1 | 4/2014 | | |
| WO | WO 2014/049297 A1 | 4/2014 | | |
| WO | WO 2014/049298 A1 | 4/2014 | | |
| WO | WO 2014/049299 A1 | 4/2014 | | |
| WO | WO 2014/049300 A1 | 4/2014 | | |
| WO | WO 2015/082659 A1 | 6/2015 | | |
| WO | WO 2015/092602 A1 | 6/2015 | | |
| WO | WO-2015186039 A1 * | 12/2015 | ........... | A61K 9/4858 |
| WO | WO 2016/026527 A1 | 2/2016 | | |

OTHER PUBLICATIONS

International Search Report and Written Opinion dated Jan. 25, 2017 in connection with PCT International Application No. PCT/US2016/058746.

J. DiGiovanna, et al.,"Systemic Retinoids in the Management of Ichthyoses and Related Skin Types", Dermatologic Therapy, vol. 26, pp. 26-38 (2013).

Aug. 25, 2020 Office Action from Japanese Patent Application No. 2018-542677. [English translation included.]

Steijlen, et al., "Topical treatment of ichthyoses and Darier's disease with 13-cis-retinoic acid—A clinical and immunohistochemical study," Archives of Dermatological Research (1993), 285(4):221-226).

* cited by examiner

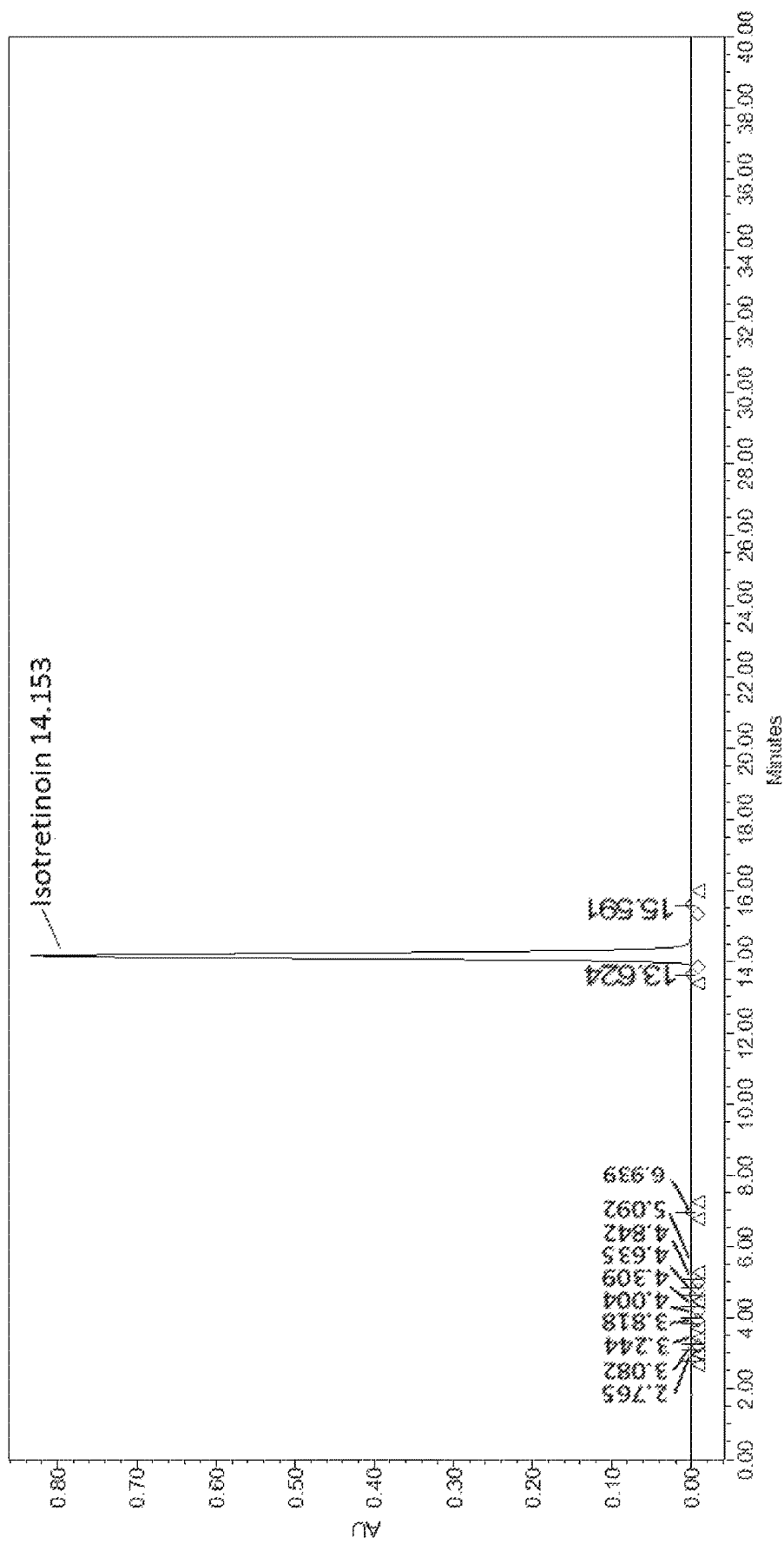

FIGURE 18

| | Formulations | | | | | %w/w |
|---|---|---|---|---|---|---|
| | PATPO3 fi | PATPO3 AA | PATPO3 AD | PATPO3 AB | PATPO3 AF | |
| Ethanol | - | 5 | - | - | - | 0.025 |
| Transcutol | - | - | - | 5 | 5 | |
| Propylene glycol | - | - | 5 | - | 5 | |
| | PATPO3 e | PATPO3 f | PATPO3 n | PATPO3 ii | PATPO3 AC | |
| Ethanol | - | - | - | - | - | 0.05 |
| Transcutol | 5 | - | 10 | 5 | - | |
| Propylene glycol | - | - | - | 5 | 5 | |
| | PATPO3 h | PATPO3 ni | PATPO3 AH | PATPO3 AI | PATPO3 Ji | |
| Ethanol | 5 | - | 5 | - | 5 | 0.10 |
| Transcutol | - | 10 | - | - | 5 | |
| Propylene glycol | 5 | - | - | 7 | - | |
| | PATPO5 | PATPO3 Ji | PATPO3 li | PATPO3 oi | PATPO3 AG | |
| Ethanol | 5 | 5 | 5 | 5 | 5 | 0.15 |
| Transcutol | - | 5 | - | - | - | |
| Propylene glycol | 5 | - | 5 | 5 | - | |
| | PATPO6 | PATPO3 gi | PATPO3 hii | PATPO3 AN | PATPO3 AO | |
| Ethanol | 5 | 5 | 5 | 10 | - | 0.20 |
| Transcutol | 5 | - | - | - | 10 | |
| Propylene glycol | - | 5 | 5 | - | - | |

ISOTRETINOIN FORMULATIONS AND USES AND METHODS THEREOF

CROSS-REFERENCE TO RELATED APPLICATIONS

This U.S. national stage application is based on PCT International Application No. PCT/US2016/058746, filed Oct. 26, 2016, which claims the benefit and priority in and to U.S. Provisional Application No. 62/248,760, filed Oct. 30, 2015, and U.S. Provisional Application No. 62/301,759, filed Mar. 1, 2016, which are both incorporated in their entirety herein by reference.

FIELD OF THE INVENTION

The present invention relates to novel isotretinoin formulations. More particularly, the present invention provides an enhanced targeted dermal delivery system for the drug isotretinoin with minimal to no systemic penetration and improved thermodynamic activity using no ethanol or a small level of ethanol relative to existing isotretinoin gel products, and methods for treatment of ichthyosis and other skin conditions using the same.

BACKGROUND OF THE INVENTION

The following discussion of the background of the invention is merely provided to aid the reader in understanding the invention and is not admitted to describe or constitute prior art to the present invention. This PCT International Application refers to various publications and publicly available products, and the disclosures from such publications and products are incorporated in their entirety herein by reference.

Ichthyosis is a heterogeneous family of at least 28 mostly genetic skin disorders, characterized by dry, thickened, scaly or flaky skin, resulting from excessive aggregation of keratinocytes (abnormal cornification). Ichthyosis and related skin type disorders include a broad spectrum of conditions differing in onset (congenital to adult onset), etiology (inherited versus acquired), intensity (mild to severe), and involvement (confined to the skin versus multisystem). In most, the barrier function of the skin is abnormal due to the abnormal process of epidermal maturation/differentiation, the quantity and quality of the *stratum corneum*, and keratinocyte proliferation kinetics. The American College of Osteopathic Dermatology estimates that 1 in 250 individuals are affected by ichthyosis vulgaris, one of the more common types of ichthyosis. While several types can be acquired, most forms of ichthyosis are considered congenital. These types include, but not limited to, Ichthyosis vulgaris, X-linked ichthyosis, Lamellar ichthyosis, Congenital Ichthyosiform Erythroderma, Epidermolytic ichthyosis, Erythrokeratodermia variablis, Pachyonychia congenital, Palmoplantar keratodermas, Harlequin type ichthyosis, Refsum disease, Conradi-Hunermann-Happle syndrome, CHILD syndrome, ichthyosis en confettis, Epidermolytic nevus, Loricrin keratoderma, Voihwinkel's disease and Sjögren-Larsson syndrome. Current lifelong therapy consists of emollients, including most standard ones which are poorly effective for treatment of severe ichthyosis, and keratolytic agents, such as alphahydroxy acids, produce burning sensations, especially in children. For congenital ichthyosis, however, there currently exist no FDA approved therapies.

Isotretinoin is a retinoid, approved by the FDA for the treatment of severe recalcitrant nodular acne. Chemically, isotretinoin is 13-cis-retinoic acid and is a derivative of vitamin A. Isotretinoin was initially developed and approved in 1982 for the treatment of acne. There are a number of ongoing studies regarding the use of isotretinoin for treatment of musculoskeletal and connective tissue inflammations, emphysema, ulcerating diseases and various cancers, namely treating cervical tumors in HIV positive women, the prevention of lung cancer in smokers and the prevention of skin cancer. Studies have been recently completed or ongoing regarding the role of isotretinoin (usually in combination with other drugs) in the treatment of neuroblastoma, recurrent prostate cancer, leukemia, high-grade glioma, head and neck cancers and multiple myeloma. Isotretinoin has also been proved to be useful in the treatment of certain dermatological conditions such as gram-negative folliculitis, recalcitrant rosacea, pyoderma faciale, generalized lichen planus, psoriasis, cutaneous lupus erythematosus, acne fulminans, and squamous cell carcinoma. It is also used for the treatment of cutaneous photoaging. Further, isotretinoin has been used in treating ichthyosis patients; however, this use has been limited to systemic delivery via oral administration, which is burdened with acute and chronic side effects to the patients, including birth defects, miscarriage, elevated cholesterol and triglycerides levels, skin dryness or stickiness, and pseudotumor cerebri. See, e.g., John J. DiGiovanna et al., "Systemic Retinoids in the Management of Ichthyoses and Related Skin Types," Dermatol. Ther., Vol. 26(1): 26-38 (January-February 2013).

Isotretinoin was originally approved as a capsule, and it is still only available in this form in the United States. Isotretinoin formulations as a gel or cream were also developed after the oral dosage form and are available in some countries outside the U.S. Additionally, a formulation known as "Isotrexin," comprising isotretinoin and erythromycin, has been marketed outside the United States. However, many topical formulations comprise high concentrations of ethanol as a solvent and penetration enhancer. High levels of ethanol, while aiding in drug permeability, can cause severe skin irritation and dryness, making many existing isotretinoin formulations unsuitable for use in treatment of skin conditions such as ichthyosis.

Therefore, there is a need for novel topical delivery systems of isotretinoin that can safely be used for dermal administration without the irritating effects of the existing topical formulations of isotretinoin but maintaining the targeted administration of the drug. Further, there is a need for novel topical delivery systems of isotretinoin in order to reduce or eradicate the risk of systemic side effects associated with isotretinoin administration.

SUMMARY OF THE INVENTION

The present invention is based on the surprising discovery of novel formulations of isotretinoin that have no ethanol or significantly lower amounts of ethanol than presently marketed isotretinoin products but enhanced targeted local delivery of isotretinoin into the epidermis and dermis. Additionally, such novel formulations of isotretinoin demonstrate minimal to no systemic penetration.

In one aspect, the present invention comprises a pharmaceutical composition comprising: isotretinoin; at least one penetration enhancer; at least one solvent; at least one viscosity modifying agent at least one preservative; and water. In another aspect, an antioxidant can also be included. In another aspect, the pharmaceutical composition is selected from the group consisting of a gel, ointment, lotion, emulsion, cream, foam, mousse, liquid, spray, suspension, dispersion and aerosol. In another aspect, the at least one penetration enhancer can be selected from the group consisting of ethanol, transcutol, and propylene glycol, or a combination thereof, and wherein the concentration of the penetration enhancer is 0% w/w but no greater than 12.5% w/w. In another aspect, the antioxidant can be BHT, N-acetylcysteine ("NAC"), or a combination thereof. In a further aspect, the antioxidant can be present in a concentration of 0.1%-30% w/w. In another aspect, the viscosity modifying agents can include cetyl alcohol, glycerol, polyethylene glycol ("PEG"), or a combination thereof. In another aspect, the at least one preservative can be selected from the group consisting of methyl parabens, propyl parabens, BHT, and a combination thereof. In yet further aspect, the solvent can be selected from the group consisting of PEG, propylene glycol, Transcutol P, ethanol, and a combination thereof. The penetration enhancers can, in some aspects, be present in a concentration of 0% w/w, 2% w/w, 5% w/w, or 10% w/w, or within the range of 0% w/w but no greater than 2% w/w. In a further aspect, the isotretinoin is present in a concentration selected from the group consisting of 0.025% w/w, 0.05% w/w, 0.10% w/w, 0.15% w/w, and 0.2% w/w. With respect to PEG, PEG can be any PEG of various molecular weights known in the art, such as those within the range of PEG 200 to PEG 4000. In a further aspect, the PEG can be a PEG (e.g., PEG 3350; PEG 4000), or combination of PEGs (e.g., PEG 1450 & PEG 3350). In another aspect, at least one humectant, which includes but not limited to urea or the like. In a further aspect, the at least one humectant can be present in a concentration of 1%-40% w/w. In another aspect, an anti-inflammatory compound can also be included. In a further aspect, the anti-inflammatory compound can be NAC, a steroid, a nonsteroidal anti-inflammatory compound, or a combination thereof. In a further aspect, the anti-inflammatory compound can be present in a concentration of 0.003%-10% w/w.

In another aspect, a pharmaceutical composition is provided comprising isotretinoin, PEG400, water, ethanol, methyl parabens, propyl parabens, PEG 4000, and BHT, wherein the concentration of ethanol is between 0% w/w and 10% w/w. The isotretinoin, in certain aspects, can be present in a concentration 0.025% w/w, 0.05% w/w, 0.10% w/w, 0.15% w/w, and 0.2% w/w; and in preferred aspects can be present in a concentration of 0.2% w/w.

In yet another aspect, a pharmaceutical composition is provided comprising about 0.05% w/w to about 0.5% w/w isotretinoin, about 60% w/w to about 65% w/w PEG 400, about 6% w/w to about 12% w/w water, about 5% w/w to about 10% w/w ethanol, about 0.05% w/w to about 0.5% w/w methyl parabens, about 0.01% w/w to about 0.05% w/w propyl parabens, about 15% w/w to about 20% w/w PEG 4000, and about 0.05% w/w to about 0.2% w/w BHT.

In a still further aspect, the present invention provides a pharmaceutical composition comprising about 0.2% w/w isotretinoin, about 63.4% w/w PEG 400, about 9% w/w water, about 10% w/w ethanol, about 0.2% w/w methyl parabens, about 0.02% w/w propyl parabens, about 17.08% w/w PEG 4000, and about 0.1% w/w BHT.

In yet another aspect, a pharmaceutical composition is provided comprising about 0.2% w/w isotretinoin, about 62.4% w/w PEG 400, about 10% w/w water, about 5% w/w ethanol, about 5% w/w transcutol, about 0.2% w/w methyl parabens, about 0.02% w/w propyl parabens, about 17.08% w/w PEG 4000, and about 0.1% w/w BHT.

In another aspect, the present invention provides a pharmaceutical composition comprising about 0.1% w/w isotretinoin, about 62.4% w/w PEG 400, about 10% w/w water, about 5% w/w ethanol, about 5% w/w transcutol, about 0.2% w/w methyl parabens, about 0.02% w/w propyl parabens, about 17.08% w/w PEG 4000, and about 0.1% w/w BHT.

In another aspect, the present invention provides a method of treating congenital ichthyosis, comprising administering to a subject in need thereof a therapeutically effective amount of a pharmaceutical composition comprising: isotretinoin; at least one penetration enhancer; at least one solvent; at least one preservative; and water; wherein the concentration of ethanol is between 0% w/w and 10% w/w. In some aspects, the pharmaceutical composition can also comprise at least one component selected from the group consisting of: an antioxidant, an emollient, a viscosity modifying agent, and a combination thereof. In some aspects, the administration can be dermal. In other aspects, the congenital ichthyosis is selected from the group consisting of Ichthyosis vulgaris, X-linked ichthyosis, Lamellar ichthyosis, Congenital Ichthyosiform Erythroderma, Epidermolytic ichthyosis, Erythrokeratodermia variablis, Pachyonychia congenital, Palmoplantar keratodermas, Harlequin type ichthyosis, Refsum disease, Conradi-Hunermann-Happle syndrome, CHILD syndrome, ichthyosis en confettis, Epidermolytic nevus, Loricrin keratoderma, Voihwinkel's disease and Sjógren-Larsson syndrome. In certain aspects, the pharmaceutical composition comprises about 0.01% w/w to about 0.5% w/w isotretinoin, about 60% w/w to about 65% w/w PEG 400, about 6% w/w to about 12% w/w water, about 5% w/w to about 12.5% w/w ethanol, about 0.05% w/w to about 0.5% w/w methyl parabens, about 0.01% w/w to about 0.05% propyl parabens, about 15% w/w to about 20% w/w PEG 4000, and about 0.05% w/w to about 0.2% w/w BHT. In other aspects, the pharmaceutical composition comprises about 0.2% w/w isotretinoin, about 63.4% w/w PEG 400, about 9% w/w water, about 10% w/w ethanol, about 0.2% w/w methyl parabens, about 0.02% w/w propyl parabens, about 17.08% w/w PEG 4000, and about 0.1% w/w BHT. In still other aspects, the pharmaceutical composition comprises about 0.2% w/w isotretinoin, about 62.4% w/w PEG 400, about 10% w/w water, about 5% w/w ethanol, about 5% w/w transcutol, about 0.2% w/w methyl parabens, about 0.02% w/w propyl parabens, about 17.08% w/w PEG 4000, and about 0.1% w/w BHT. In still further aspects, the pharmaceutical composition comprises about 0.1% w/w isotretinoin, about 62.4% w/w PEG 400, about 10% w/w water, about 5% w/w ethanol, about 5% w/w transcutol, about 0.2% w/w methyl parabens, about 0.02% w/w propyl parabens, about 17.08% w/w PEG 4000, and about 0.1% w/w BHT. In a further aspect, the subject is human.

In another aspect, a pharmaceutical composition comprises isotretinoin, and at least one solvent. In a further aspect, the pharmaceutical composition further comprises at least one penetration enhancer. In yet further aspect, the at least one penetration enhancer is selected from the group consisting of ethanol, transcutol, propylene glycol, and a combination thereof. In a further aspect, the at least one penetration enhancer is ethanol, and the concentration of ethanol is no greater than 2% w/w. In a further aspect, the pharmaceutical composition further comprises 0% w/w ethanol and/or 0% w/w water. In a further aspect, the pharmaceutical composition further comprises at least one preservative. In yet a further aspect, the at least one preservative is selected from the group consisting of methyl parabens, propyl parabens, BHT, and a combination thereof. In yet a further aspect, the at least one solvent is selected from the group consisting of polyethylene glycol (PEG), propylene glycol, and a combination thereof. In a further aspect, the pharmaceutical composition is formulated as a gel, ointment, lotion, emulsion, cream, foam, mousse, liquid, spray, suspension, dispersion or aerosol.

In a further aspect, the pharmaceutical composition further comprises at least one antioxidant. The at least one antioxidant can be NAC, BHT, or a combination thereof. In a further aspect, the concentration of NAC is at least 0.1% w/w but no greater than 30% w/w. In a further aspect, an anti-inflammatory compound can also be included, wherein the anti-inflammatory compound can be NAC, a steroid, a nonsteroidal anti-inflammatory compound, or a combination thereof. In yet a further aspect, the anti-inflammatory compound can be present in a concentration of 0.003%-10% w/w.

In a further aspect, the pharmaceutical composition further comprises at least one humectant. The at least one humectant can be urea, and the concentration of urea can be at least 1% w/w but no greater than 40% w/w. In a further aspect, the pharmaceutical composition further comprises at least one viscosity modifying agent. The at least one viscosity modifying agent can be glycerol, PEG, or a combination thereof.

In another aspect, a pharmaceutical composition comprising isotretinoin, PEG 400, PEG 3350, and BHT. In a further aspect, the pharmaceutical composition further comprises methyl parabens and/or propyl parabens. In a further aspect, the isotretinoin is present in the concentration of about 0.01% to about 0.2% w/w. In a further aspect, the isotretinoin is present in the concentration of about 0.025% to about 0.2% w/w. In a further aspect, the pharmaceutical composition further comprises ethanol, wherein the concentration of ethanol is no greater than 2% w/w. Alternatively, in a further aspect, the pharmaceutical composition contains 0% w/w ethanol. In a further aspect, the pharmaceutical composition further comprises NAC.

In another aspect, a pharmaceutical composition comprising isotretinoin, PEG 400, PEG 3350, PEG 1450, and BHT. In a further aspect, the pharmaceutical composition further comprises methyl parabens and/or propyl parabens. In a further aspect, the isotretinoin is present in the concentration of about 0.01% to about 0.2% w/w. In a further aspect, the isotretinoin is present in the concentration of about 0.025% to about 0.2% w/w. In a further aspect, the pharmaceutical composition further comprises ethanol, wherein the concentration of ethanol is no greater than 2% w/w. Alternatively, in a further aspect, the pharmaceutical composition contains 0% w/w ethanol. In a further aspect, the pharmaceutical composition further comprises NAC.

In another aspect, a pharmaceutical composition comprising about 0.01% w/w to about 0.6% w/w isotretinoin, about 67% w/w to about 70% w/w PEG 400, 0% w/w to about 2% w/w ethanol, about 0.2% w/w methyl parabens; about 0.02% w/w propyl parabens, about 14% w/w to about 30% w/w PEG 3350, about 0% to about 15% w/w PEG 1450, and about 0.1% w/w BHT. In a further aspect, wherein the amount of isotretinoin is about 0.025% to about 0.6%.

In another aspect, a pharmaceutical composition comprising about 0.01% w/w to about 0.6% w/w isotretinoin, about 67% w/w to about 70% w/w PEG 400, 0% w/w to about 2% w/w ethanol, about 14% w/w to about 30% w/w PEG 3350, about 0% to about 15% w/w PEG 1450, and about 0.1% w/w BHT. In a further aspect, wherein the amount of isotretinoin is about 0.025% to about 0.6%.

In another aspect, a method of treating congenital ichthyosis, comprising administering to a subject in need thereof a therapeutically effective amount of a pharmaceutical composition comprising isotretinoin, and at least one solvent. In a further aspect, the at least one solvent is 0% w/w but no greater than 2% w/w ethanol and/or PEG. In a further aspect, the pharmaceutical composition further comprises at least one antioxidant, wherein the at least one antioxidant is BHT, NAC, or a combination thereof. In a further aspect, the administration is dermal. In a further aspect, the congenital ichthyosis is selected from the group consisting of Ichthyosis vulgaris, X-linked ichthyosis, Lamellar ichthyosis, Congenital Ichthyosiform Erythroderma, Epidermolytic ichthyosis, Erythrokeratodermia variablis, Pachyonychia congenital, Palmoplantar keratodermas, Harlequin type ichthyosis, Refsum disease, Conradi-Hunermann-Happle syndrome, CHILD syndrome, ichthyosis en confettis, Epidermolytic nevus, Loricrin keratoderma, Voihwinkel's disease, and Sjógren-Larsson syndrome. In a further aspect, the subject is human.

In another aspect, a method of treating congenital ichthyosis, comprising administering to a subject in need thereof a therapeutically effective amount of a pharmaceutical composition, the pharmaceutical composition comprising about 0.01% w/w to about 0.6% w/w isotretinoin, about 67% w/w to about 70% w/w PEG 400, about 0% w/w to about 2% w/w ethanol, about 0.2% w/w methyl parabens; about 0.02% w/w propyl parabens, about 14% w/w to about 30% w/w PEG 3350, about 0% to about 15% w/w PEG 1450, and about 0.1% w/w BHT. In a further aspect, wherein the amount of isotretinoin is about 0.025% to about 0.6%. In a further aspect, wherein the amount of isotretinoin is about 0.025% to about 0.2%. In a further aspect, the subject is human.

As used herein, "transdermal" administration means transport of an agent through or by way of the skin for introduction into systemic circulation.

As used herein, "dermal" administration means transport of an agent across the *stratum corneum* and into the dermis and/or epidermis for treatment of a topical skin disorder (such as congenital ichthyosis) that responds to local, non-systemic administration of an agent. It will be appreciated that some of the agent intended for dermal therapy can be transdermally administered, however typically not in an amount sufficient for therapy.

As used herein, "therapeutically effective amount" means an amount of isotretinoin sufficient to prevent or reduce the symptoms associated with a disease or condition (such as congenital ichthyosis) and/or lessen the severity of the disease or condition. A therapeutically effective amount is understood to be in context to the condition being treated, where the actual effective amount is readily discerned by those of skill in the art.

As used herein, "isotretinoin" refers to isotretinoin in the form of a free acid or its pharmaceutically acceptable salts, such as alkali metal salts. Isotretinoin is 13-cis-retinoic acid. Tretinoin (all-trans retinoic acid) and isotretinoin are geometric isomers and show reversible interconversion in vivo. The administration of one isomer can give rise to another. Other major metabolites of isotretinoin such as 4-oxo-isotretinoin and its geometrical isomer 4-oxo-tretinoin are also contemplated in the term "isotretinoin."

As used herein, "permeation rate" means the rate of passage of the drug through the skin. Permeation rate is calculated as the slope of the linear portion of the cumulative amount of drug permeated per $cm^2$ over time.

As used herein, "transport rate" refers to the rate of passive drug transport across human skin as governed by Fick's Law of diffusion. The mass transport equation is given as: $J=1/A(dM/dt)=P\Delta C\,dt$ where J is flux ($\mu g\,cm^2/hr$), A is cross sectional area of the skin membrane (cm²), P is the apparent permeability coefficient (cm hr), ΔC is the concentration gradient across the membrane, and (dM/dt) is the mass transport rate.

BRIEF DESCRIPTION OF THE FIGURES

FIGS. 12A & 12B are chromatograms showing stability of the isotretinoin formulation PATPO3 AN containing 0.2% w/w isotretinoin, overlaid with PATPO3 AN placebo at t=4 weeks following storage at 40° C., between 2 and 17 minutes.

FIG. 18 is a table listing PEG ointment formulations for each of the possible penetration enhancer options selected for the initial permeation studies discussed further below. The penetration enhancer compositions, expressed as % w/w, of the PEG ointment formulations, are shown with the circles indicating those selected for the in vitro permeation and penetration experimentation.

DETAILED DESCRIPTION OF THE INVENTION

Figure 1:
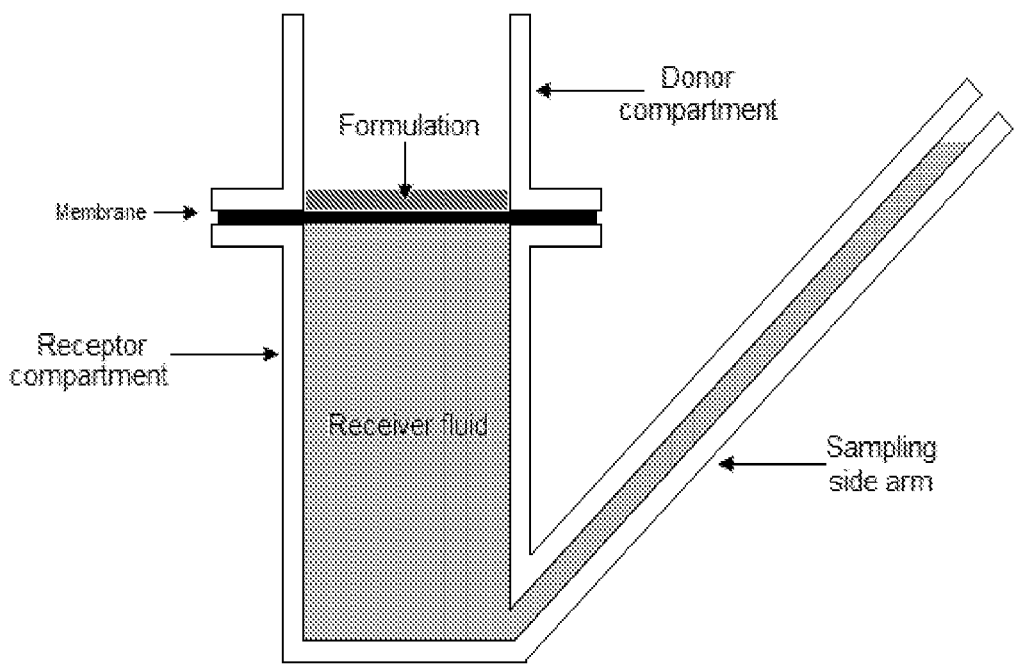
FIG. 1 is a schematic showing a Franz cell as used in the in vitro drug transport experiments described herein, including a donor component, a receptor component, and a sampling side arm.
Figure 2:
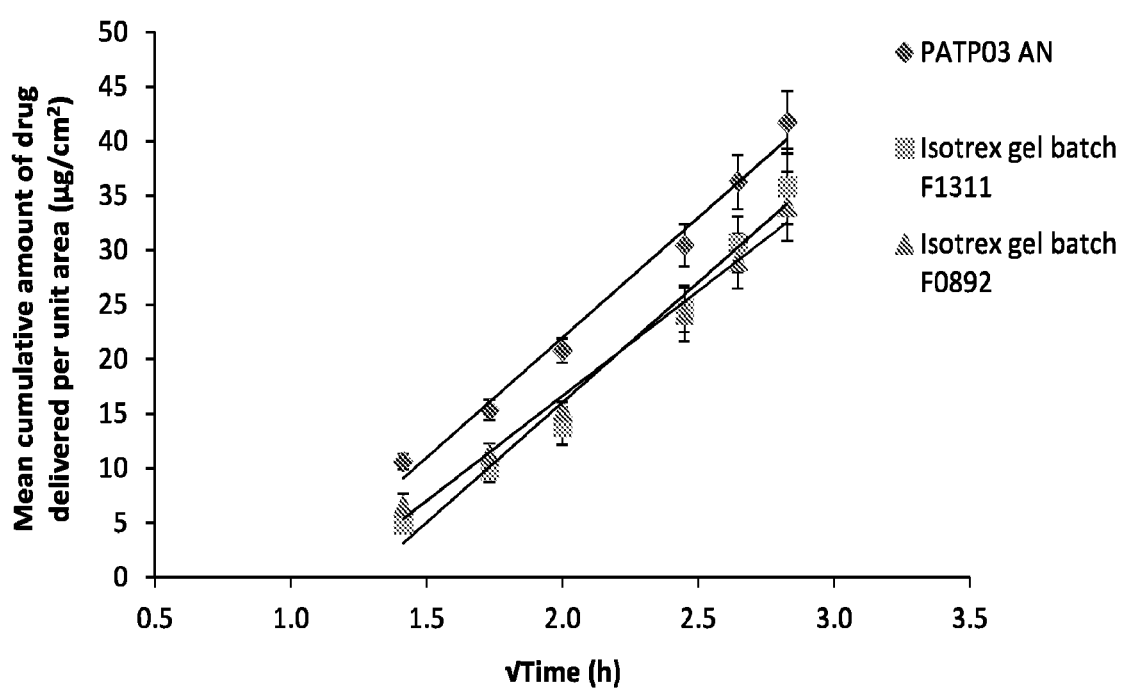
FIG. 2 is a line graph showing the mean cumulative amount of isotretinoin (µg/cm2) delivered from a claimed composition ("PATPO3 AN") as compared to Isotrex gel 0.05% (batches: F1311 and F0892), through a silicone membrane between 2 and 8 h (time represented as √time, mean±SE, 5≤n≤6).

The present invention is directed to novel targeted formulations of isotretinoin that result in increased penetration of the dermal layers with minimal to no systemic penetration and without increasing the concentration of ethanol (or eliminating ethanol altogether) relative to the presently marketed products, and methods of treatment of ichthyosis using the same.

Dermal delivery of drugs provides many advantages; primarily, such a means of delivery is a comfortable, convenient and noninvasive way of administering drugs. The variable rates of absorption and metabolism encountered in oral treatment are avoided, and other inherent inconveniences, e.g., gastrointestinal irritation and the like, are eliminated as well. Further, significant side effects associated with delivery to other areas (e.g., to subdermal or extradermal structures and/or to tissues other than dermis) are avoided.

Skin, however, is a structurally complex membrane. Molecules moving from the environment into and through intact skin must first penetrate the *stratum corneum* and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the *stratum corneum*, which present the primary barrier to absorption of topical compositions or transdermally administered drugs. The *stratum corneum* is a thin layer of dense, highly keratinized cells approximately 10-15 microns thick over most of the body. With many drugs, the rate of permeation through the skin is extremely low without the use of some means to enhance the permeability of the skin.

Numerous chemical agents have been studied as a means of increasing the rate at which a drug penetrates through the skin. As will be appreciated by those in the field, chemical enhancers are compounds that are administered along with the drug (or in some cases the skin can be pretreated with a chemical enhancer) in order to increase the permeability of the *stratum corneum*, and thereby provide for enhanced penetration of the drug through the skin. Ideally, such chemical penetration enhancers or "permeation enhancers," as the compounds are referred to herein, are compounds that are innocuous and serve merely to facilitate diffusion of the drug through the *stratum corneum*. The permeability of many therapeutic agents with diverse physicochemical characteristics can be enhanced using these chemical enhancement means. However, there are skin irritation, dryness and sensitization problems associated with high levels of certain enhancers, such as ethanol.

The novel formulations herein are surprisingly shown herein to have improved thermodynamic activity vis-a-vis the presently available isotretinoin topical gel formulations, while having none or decreased levels of irritating ethanol agents. Typically, the influence of ethanol on drug permeability is concentration dependent, with the percutaneous absorption being optimized at a level of greater than 50% w/w ethanol. In fact, the existing Isotrex gel products have over 95% w/w ethanol. The aspects of isotretinoin ointment formulations, though, three representative formulations of which are shown in Table 1 below, each comprise less than 10% w/w ethanol. Thus, these novel formulations enhance the delivery of isotretinoin into the epidermis and dermis, with little chance of causing skin irritation and dryness.

TABLE 1

| Component: | % w/w Formulation 1 (PATPO3 AN) | % w/w Formulation 2 (PATPO6) | % w/w Formulation 3 (PATPO3 AI) |
|---|---|---|---|
| Isotretinoin | 0.2 | 0.2 | 0.1 |
| PEG 400 | 63.4 | 62.4 | 60.4 |
| Water | 9 | 10 | 10 |
| Ethanol | 10 | 5 | 0 |
| Glycerol | 0 | 0 | 5 |
| Propylene Glycol | 0 | 0 | 7 |
| Methyl Parabens | 0.2 | 0.2 | 0.2 |

TABLE 1-continued

| Component: | % w/w Formulation 1 (PATPO3 AN) | % w/w Formulation 2 (PATPO6) | % w/w Formulation 3 (PATPO3 AI) |
|---|---|---|---|
| Propyl Parabens | 0.02 | 0.02 | 0.02 |
| PEG 4000 | 17.08 | 17.08 | 17.18 |
| BHT | 0.1 | 0.1 | 0.1 |
| Transcutol | 0 | 5 | 0 |
| Total | 100 | 100 | 100 |

The novel preparations described herein are, in some aspects, formulated as a gel, ointment, lotion, emulsion, cream, foam, mousse, liquid, spray, suspension, dispersion or aerosol, or any other vehicle known to those of skill in the art. In preferred aspects, the preparations are formulated as a gel, ointment, foam, or cream.

A lotion can contain finely powdered substances that are insoluble in the dispersion medium through the use of suspending agents and dispersing agents. Alternatively, lotions can have dispersed phase liquid substances that are immiscible with the vehicle and are usually dispersed by means of emulsifying agents or other suitable stabilizers. In some aspects, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

Creams can contain emulsifying agents and/or other stabilizing agents. In one aspect, the formulation is in the form of a cream having a viscosity of greater than 1000 centistokes, typically in the range of 20,000-50,000 centistokes.

The basic difference between a cream and a lotion is the viscosity, which is dependent on the amount/use of various oils and the percentage of water used to prepare the formulations. Creams are typically thicker than lotions, can have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., PEG ointments). Pastes typically differ from ointments in that they contain a larger percentage of solids. Pastes are typically more absorptive and less greasy that ointments prepared with the same components.

Some emulsions can be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, can also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams can include an emulsion in combination with a gaseous propellant. The gaseous propellant can include primarily of hydro fluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

The novel preparations are, in particularly preferred aspects, formulated as ointments. Ointments are semisolid preparations that are typically based on petrolatum or other petroleum derivatives. The specific ointment foundation to be used, as will be appreciated by those skilled in the art, is one that will provide for optimum drug delivery, and, preferably, will provide for other desired characteristics as well, e.g., emolliency or the like. As with other carriers or vehicles, an ointment foundation should be inert, stable, nonirritating and nonsensitizing. As explained in *Remington: The Science and Practice of Pharmacy*, 20$^{th}$ edition (Lippincott Williams & Wilkins, 2000), ointment foundations can be grouped in four classes: oleaginous, emulsifiable, emulsion, and water-soluble. Oleaginous ointment foundations include, for example, vegetable oils, fats obtained from animals, and semisolid hydrocarbons obtained from petroleum. Emulsifiable ointment foundations, also known as absorbent ointment foundations, contain little or no water and include, for example, hydroxystearin sulfate, anhydrous lanolin and hydrophilic petrolatum. Emulsion ointment foundations are either water-in-oil (W/O) emulsions or oil-in-water (O/W) emulsions, and include, for example, cetyl alcohol, glyceryl monostearate, lanolin and stearic acid. Preferred water-soluble ointment foundations are prepared from PEGs of varying molecular weight.

Various additives, known to those skilled in the art, can, in some aspects, be included in the ointments. For example, solvents, including relatively small amounts of alcohol, can be used to solubilize certain drug substances. Other optional additives include opacifiers, antioxidants, fragrance, colorant, gelling agents, thickening agents, stabilizers, surfactants and the like. Other agents can also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

In some aspects, the ointments can also include penetration enhancing agents. Examples of classes of enhancers include, but are not limited to, fatty acids, both saturated and unsaturated; fatty alcohols; bile acids; nonionic surfactants, including esters of fatty acids, fatty (long-chain alkyl or alkenyl) esters of monohydric alcohols, diols, and polyols, diols and polyols that are both esterified with a fatty acid and substituted with a polyoxyalkylene, polyoxyalkylene fatty acid esters, polyoxyalkylene fatty ethers, polyoxyalkylene fatty ethers, and polyglyceryl fatty acid esters; amines; amides; N-alkyl-azacycloalkanones and N-alkyl-azacycloalkenones; hydrocarbon solvents; terpenes; lower alkyl esters; cyclodextrin enhancers; nitrogen-containing heterocycles; sulfoxides; and urea and its derivatives.

Specific examples of suitable enhancing agents include ethers such as diethylene glycol monoethyl ether (available commercially as Transcutol®, Gattefosse SA) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as PEG, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as dimethylsulfoxide and decylmethylsulfoxide can also be used, but are less preferred. *Percutaneous Penetration Enhancers*, eds. Smith et al. (CRC Press, 1995) provides an excellent overview of the field and further information concerning possible secondary enhancers for use in conjunction with the present invention.

EXAMPLES

The present invention, thus generally described, will be understood more readily by reference to the following examples, which are provided by way of illustration and are not intended to be limiting of the exemplary formulations and methods discussed herein.

Example 1

In Vitro Drug Transport Assessment

To assess the transport profiles of isotretinoin from certain formulations that included those described in Table 1, an in vitro drug transport investigation was performed across a synthetic membrane. The transport of the drug from the selected formulations was compared using method based on the principles of the FDA's SUPAC-SS guidelines [FDA (CDER), 1997, Guidance for industry—SUPAC-SS Nonsterile Semisolid Dosage Form, Scale-up and post approval changes: Chemistry, manufacturing and controls; in vitro drug transport testing and in vivo bioequivalence documentation].

A total of six formulations at each of the five concentrations of isotretinoin (0.025, 0.05, 0.10, 0.15 and 0.20% w/w, were assessed (each at n=6) herein and compared against the results of the comparator product, Isotrex gel 0.05%. A total of two batches of Isotrex gel were used in this experiment, which were both tested in six replicates. Furthermore, one batch of Isotrex gel 0.05% was tested concurrently in a subset of cells (n=3) as a control to assess the run-to-run method variability. The following parameters were employed: Receiver fluid: 2% Bruj in 20% ethanol: 80% PBS with 0.01% BHA; synthetic membrane: silicone; time points: t=0, 1, 2, 3, 4, 6, 7, 8, and 24 h; dose: greater than 0.3 g.

Figure 5:
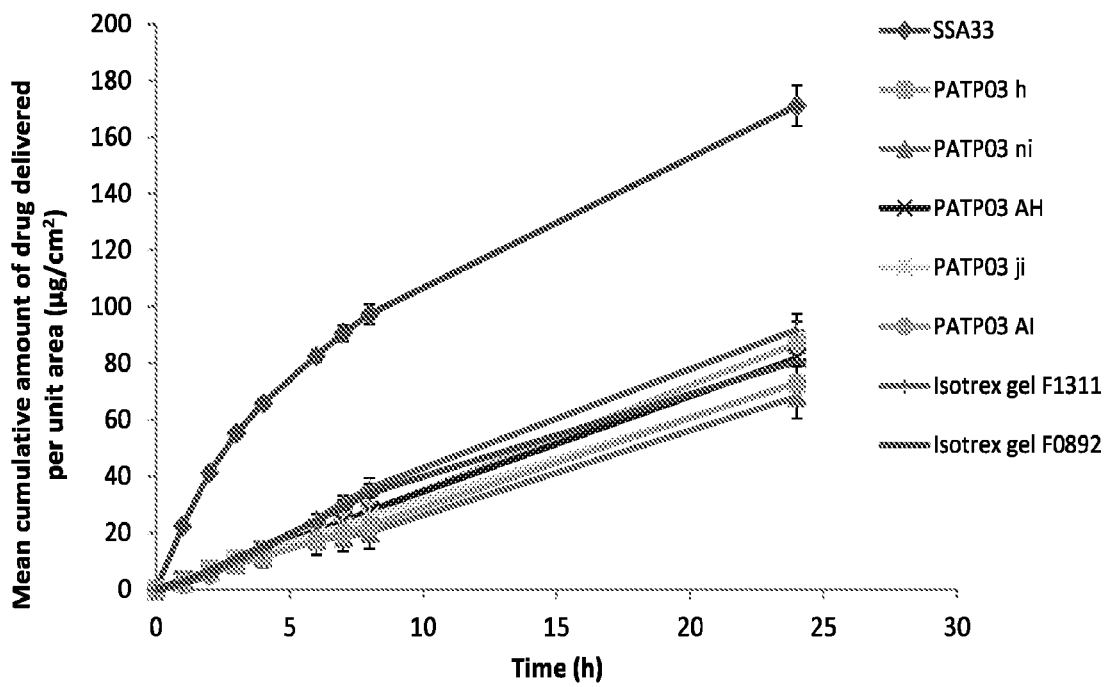
FIG. 5 is a line graph showing the mean cumulative amount of isotretinoin delivered per unit area (m/cm²) over a 24 h experimental period through silicone membrane from PEG ointments and gel including isotretinoin at 0.10%, compared to that from two batches of Isotrex gel 0.05% (mean±SE, n≥5).
Figure 6:
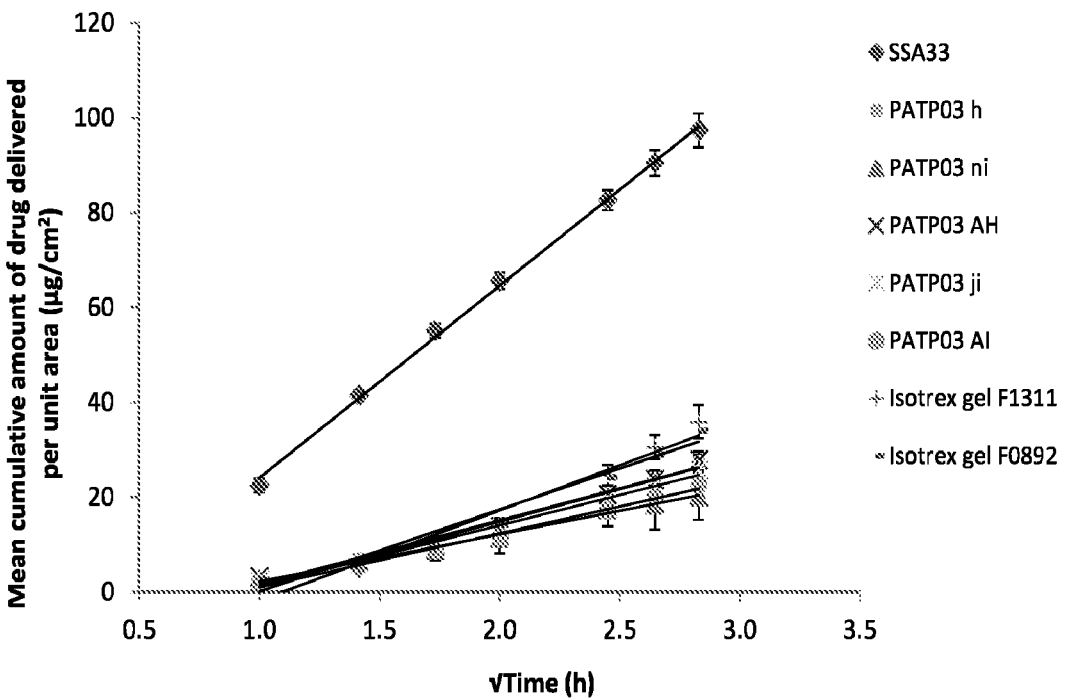
FIG. 6 is a line graph showing the mean cumulative amount per unit area of isotretinoin (µg/cm²) delivered from PEG ointments and gel including isotretinoin at 0.10% through silicone membrane between 1 and 8 h (time represented as √time), compared to that from two batches of Isotrex gel 0.05% (mean±SE, n≥5).
Figure 7:
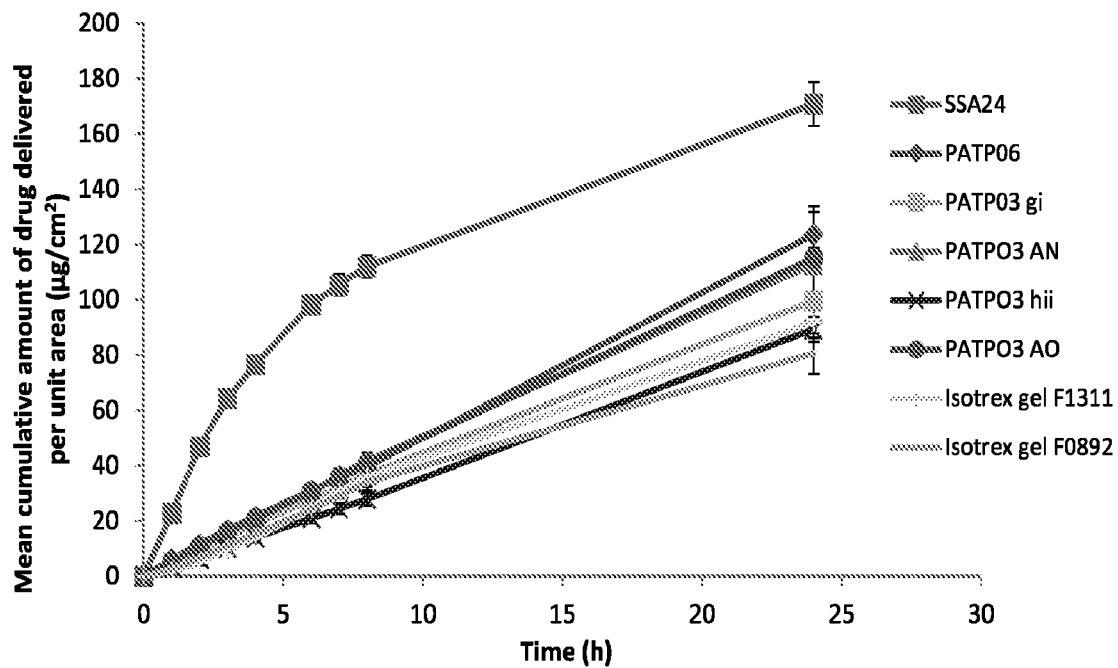
FIG. 7 is a line graph showing the mean cumulative amount of isotretinoin delivered per unit area (µg/cm²) over a 24 h experimental period through silicone membrane from PEG ointments and gel including isotretinoin at 0.20%, compared to that from two batches of Isotrex gel 0.05% (mean±SE, n≥5).
Figure 8:
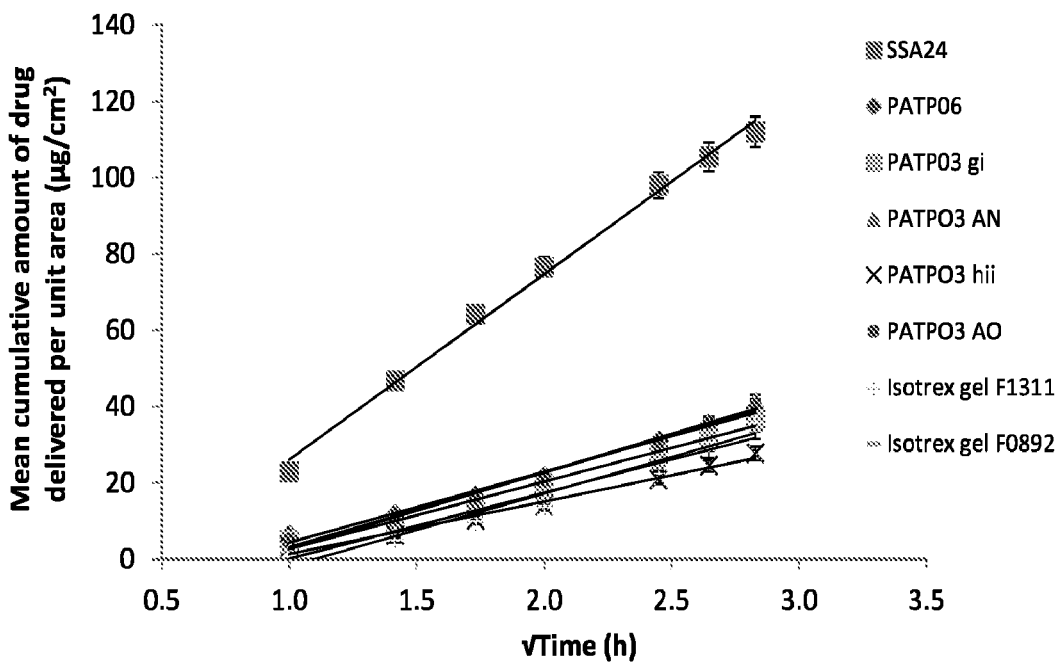
FIG. 8 is a line graph showing the mean cumulative amount per unit area of isotretinoin (m/cm²) delivered from PEG ointments and gel including isotretinoin at 0.20% through silicone membrane between 1 and 8 h (time represented as √time), compared to that from two batches of Isotrex gel 0.05% (mean±SE, n≥5).

FIGS. 5 and 7 depict the transport of the drug from the claimed formulations at various concentrations of isotretinoin, compared to that from Isotrex gel 0.05% (both batches, F0892 and F1311). The steady state transport of isotretinoin across silicone membrane was seen from 1 h after dosing, for all the formulations assessed. FIGS. 6 and 8 highlight the steady state drug transport between 1 and 8 h (presented as a √time, as recommended in the SUPAC guidelines) from the tested prototype formulations at various concentrations of isotretinoin, compared to that from Isotrex gel 0.05%. The calculated transport rates (μg/cm2/√h) of isotretinoin from all the formulations across silicone are reported in Tables 2 and 3.

TABLE 2

| Isotretinoin % (w/w) | 0.025% | Transport rate | 0.05% | Transport rate | 0.10% | Transport rate | 0.15% | Transport rate | 0.20% | Transport rate |
|---|---|---|---|---|---|---|---|---|---|---|
| Formulations | SSA37 | 7.74 ± 0.66 | SSA36 | 22.40 ± 2.31 | SSA33 | 40.52 ± 1.37 | SSA31 | 53.22 ± 4.48 | SSA24 | 48.62 ± 5.92 |
| | PATPO3 AF | 6.40 ± 1.38 | PATPO3 n | 8.04 ± 0.43 | PATPO3 AH | 13.67 ± 1.83 | PATPO3 li | 18.48 ± 3.29 | PATPO3 AN | 20.06 ± 3.61 |
| | PATPO3 AA | 6.11 ± 1.02 | PATPO3 AC | 7.38 ± 0.31 | PATPO3 h | 13.48 ± 2.60 | PATPO3 Ji | 16.44 ± 1.46 | PATPO3 AO | 19.55 ± 2.00 |
| | PATPO3 AD | 4.46 ± 0.70 | PATPO3 e | 6.72 ± 0.44 | PATPO3 Ji | 12.80 ± 1.88 | PATPO3 oi | 13.58 ± 1.99 | PATPO6 | 18.55 ± 3.42 |
| | PATPO3 AB | 3.47 ± 0.65 | PATPO3 f | 5.43 ± 0.79 | PATPO3 Al | 11.36 ± 1.51 | PATPO5 | 12.91 ± 1.15 | PATPO3 gi | 17.65 ± 1.52 |
| | PATPO3 fi | 3.28 ± 0.33 | PATPO3 ii | 5.00 ± 0.88 | PATPO3 ni | 9.91 ± 1.88 | PATPO3 AG | 12.80 ± 1.88 | PATPO3 hii | 13.77 ± 2.39 |

TABLE 3

Isotrex gel 0.05%

| Batch no. F1131 | Batch no. F0892 |
|---|---|
| 19.09 ± 3.86 | 17.30 ± 5.59 |

The statistical analysis of these results indicates that all the prototype gel formulations provided surprisingly and significantly ($p \leq 0.05$) greater transport rate of isotretinoin compared to Isotrex gel 0.05%, with the exception of SSA37 (0.025%). For the PEG ointments including 0.1, 0.15 and 0.2% of isotretinoin, the transport of the drug was observed to be similar ($p > 0.05$) to that determined when using Isotrex gel 0.05%. In contrast, the Isotrex gel was found to provide a greater transport with respect to the PEG ointments containing 0.025 and 0.05% of isotretinoin, which is unsurprising considering that the Isotrex gel includes mainly ethanol, the evaporation of which causes the drug thermodynamic activity, and so the flux, to increase over the duration of the experiment.

Example 2

In Vitro Permeation and Penetration Assessments

Following completion of the transport experiment, quantification of isotretinoin on the surface of the skin and the skin strata was performed as described below:

Commonly, in vitro skin permeation experiments involve the use of a diffusion cell designed to mimic the physiological and anatomical conditions of skin in situ. The model used in this experiment was the Franz diffusion cell as described in FIG. 1 (where the synthetic membrane was replaced with human dermatomed skin). The subcutaneous fat was removed mechanically and the skin was dermatomed to a thickness of 400±100 μm using a Nouvag TCM 3000 cutter. Human dermatomed skin was positioned between the donor and receptor compartment of a Franz cell (FIG. 1) with the *Stratum corneum* side up. For each active formulation up to 4 repetitions per formulation per skin donor (3 donors) were performed; however, only a single repetition was performed for the placebo formulation (n=1).

FIG. 18 (which was Table 4 in the specification as filed) lists the PEG ointment formulations for each of the possible penetration enhancer options selected for the initial permeation studies. The penetration enhancer compositions, expressed as % w/w, of the PEG ointments, are shown with the circles indicating those selected for the in vitro permeation and penetration experimentation.

The following parameters were employed for the in vitro skin permeation experiment:

Receiver fluid: 2% Brij in 20% ethanol: 80% PBS with 0.01% BHA.

Time points: t=0, 6, 24 and 48 h.

Membrane: human dermatomed skin with a thickness of 400±100 μm (from three different donors).

Dose: ~10 mg/cm$^2$).

The following procedures were employed: Franz diffusion cells with an average surface area of approximately 0.6 cm$^2$ and a volume of approximately 2.0 mL were employed. First, prior to dosing, the integrity of the skin was assessed as follows: (a) Dermatomed skin (from three donors) was mounted between the donor and receiver compartments and the cells were sealed together using Parafilm® and clips. (b) The donor and receiver chambers were filled with PBS solution and a small magnetic follower was placed in the receiver compartment. (c) Cells were equilibrated in a water bath ensuring a membrane temperature of 32° C. for 30 min (water bath temperature of 37° C.). (d) The resistance of the skin in each Franz cell was measured using the LCR 6401 Databridge (SOP 3118). (e) The electrodes were placed in the receiver compartment through the sampling arm and the donor chamber. (f) The LCR was set at 100 Hz and set to 'R' for resistance. (g) Cells with a resistance below the acceptable limits were discarded and remounted. Acceptable limits are defined according to the measurement of controls for dermatomed skin, where the skin has been deliberately perturbed. Cells with greater than twice the resistance (KΩ) of the control were considered acceptable and selected for the Franz cell permeation experiment.

Second, following skin integrity testing the PBS solution was removed from each compartment and the receiver compartment of acceptable cells was filled with receiver fluid (2% Brij in 20% ethanol: 80% PBS with 0.01% BHA). Each cell was then equilibrated to ensure a surface temperature of 32° C. (external skin surface temperature) for at least 30 min prior to dosing (water bath temperature of 37° C.). Third, a positive displacement pipette was used to apply the formulation (~8 mg) to the plunger of a 1 mL syringe. The formulation (6-7 mg) was applied to the skin surface and spread over the diffusion area using the plunger. Prior to and after application the weight of the plunger was recorded and the amount per cell was calculated. Fourth, receiver fluid (200 µL) was removed at the following time points t=0, 6, 24 and 48 h and transferred to a HPLC vial for analysis using HPLC. Fifth, fresh pre-warmed receiver fluid (200 µL) was used to replace the receiver fluid removed at each time point. Sixth, following the final time point (48 h), the Franz cells were dismantled and the drug was recovered from the skin.

Isotretinoin was recovered from the surface of the skin as follows: (i) After dismantling the donor chamber from the Franz cell, one dry cotton swab was used to remove any residual formulation from the surface of the skin and the swab placed into the 7 mL vial; (ii) A second swab was immersed into the extraction diluent (90:10-ethanol:water) and used to swab the surface of the skin; this swab will then be placed into the vial containing the first swab; (iii) The final swab was used dry to swab the surface of the skin and then placed into the glass vial containing the two other swabs; (iv) An initial tape strip (using D-Squame®) from the surface of the skin was also placed in with the cotton wool swabs and 2 mL of extraction diluent (90:10 ethanol:water) was added; (v) Each vial was then shaken on an orbital shaker at ambient temperature for at least 16-20 h in the extraction solvents to facilitate the extraction; (vi) Following the extraction procedure, the extraction diluent was removed from the vials and centrifuged at 13,000 rpm for 10 min to remove all un-dissolved materials and particles; and (vii) The supernatant from each sample was then transferred to a HPLC vial and analysed using HPLC.

The following procedure was then used to recover isotretinoin from the *Stratum corneum*: (i) A total of five further tape strips (using D-Squame®) from the surface of the skin were taken, placed into a glass vial and 2 mL of extraction diluent (90:10-ethanol:water) was added to it; (ii) The vials from Step (i) were shaken on an orbital shaker at ambient laboratory temperature for 16 to 20 h; (iii) Following the extraction procedure (Step (ii)), the extraction solution was removed from the vials and centrifuged at 13,000 rpm for 10 min to remove all un-dissolved materials and particulates; and (iv) The supernatant was placed into vials for analysis by HPLC.

As described in greater detail below, the remaining epidermis and dermis were processed as follows: (i) The remaining epidermis (after removing the *Stratum corneum* by using 5 tape strips) was heat-separated from the dermis by dry heating at 60 degrees Celsius for 2 minutes; (ii) The epidermal and dermal layers were placed into individual glass vials and 2 mL of extraction solvent (90:10-ethanol: water) was added to these vials; (iii) The vials from Step (ii) were shaken on an orbital shaker at ambient laboratory temperature for 16 to 20 h; (iv) Following the extraction procedure (Step (iii)), the extraction solution was removed from the vials and centrifuged at 13,000 rpm for 10 min to remove all un-dissolved materials and particulates; and (v) The supernatant was placed into vials for analysis by HPLC.

The data was interpreted as follows: (i) Data was manually transcribed into Excel spreadsheets. The levels of isotretinoin detected in the receiver fluid and skin strata were calculated from the respective calibration standards; (ii) The total amount (µg) of isotretinoin per volume sampled was calculated (total amount/volume sampled=µg/mL×volume sampled); (iii) The total amount (µg) of isotretinoin recovered at each time point as then calculated (total amount=µg/mL×total volume of each Franz cell); (iv) The cumulative amount (µg) of isotretinoin was calculated by adding the total amount (µg, Step (iii)) at each time point with the total amount withdrawn (µg) from each of the previous time points (Step (ii)); (v) The cumulative amount per unit area of isotretinoin (µg/cm2) was calculated by dividing the cumulative amount (µg, Step (iv)) by the diffusion area (µg/cm2=cumulative amount (µg)/diffusion area); (vi) Any outliers were rejected according to internal procedures; (vii) The transport rate of isotretinoin across silicone membrane from all the formulations tested was calculated as slope of the linear portion of the profile "cumulative amount permeated of drug permeated per cm2 vs. √t (as recommend per SUPAC guidelines); and (viii) The total amount (µg) of isotretinoin in each of the skin matrices was calculated (total amount=µg/mL×extraction dilution).

Statistical analysis of data was performed using statistical package for social science (SPSS) version 19.0 (SPSS Inc., USA). Such analysis was carried out to determine any significant difference in the amount of isotretinoin released from each test formulations and comparator product. Furthermore, statistical analysis was carried out to identify significant difference in the levels of drug recovered from surface, *Stratum corneum*, epidermis and dermis and receiver fluid at 48 h, from each of the tested formulations compared to the Isotrex gel 0.05%.

Figure 9:
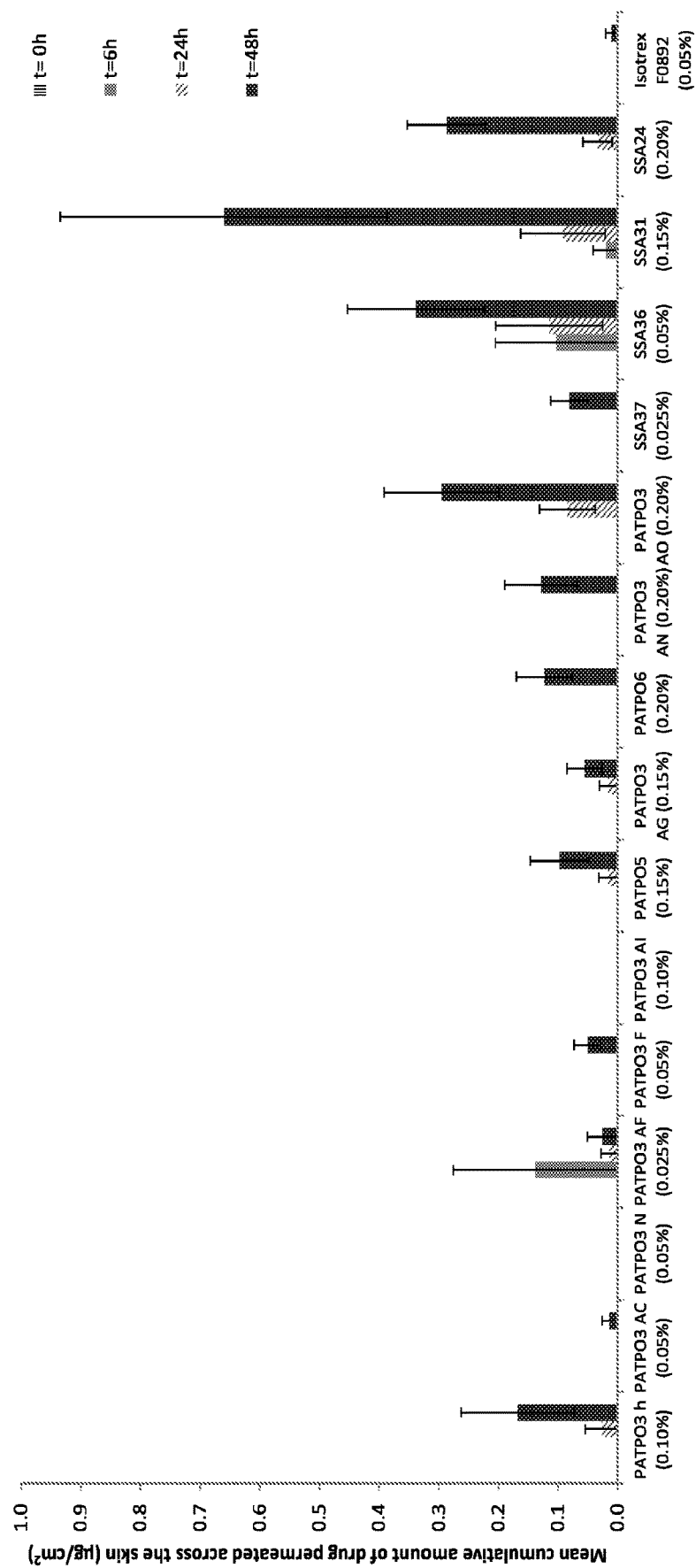
FIG. 9 is a bar graph showing the mean cumulative amount of isotretinoin permeated across the skin (µg/cm²) into the receiver fluid following the application of certain tested formulations and comparator product, Isotrex gel 0.05% (mean±SE, 10≤n≤12).
Figure 10:
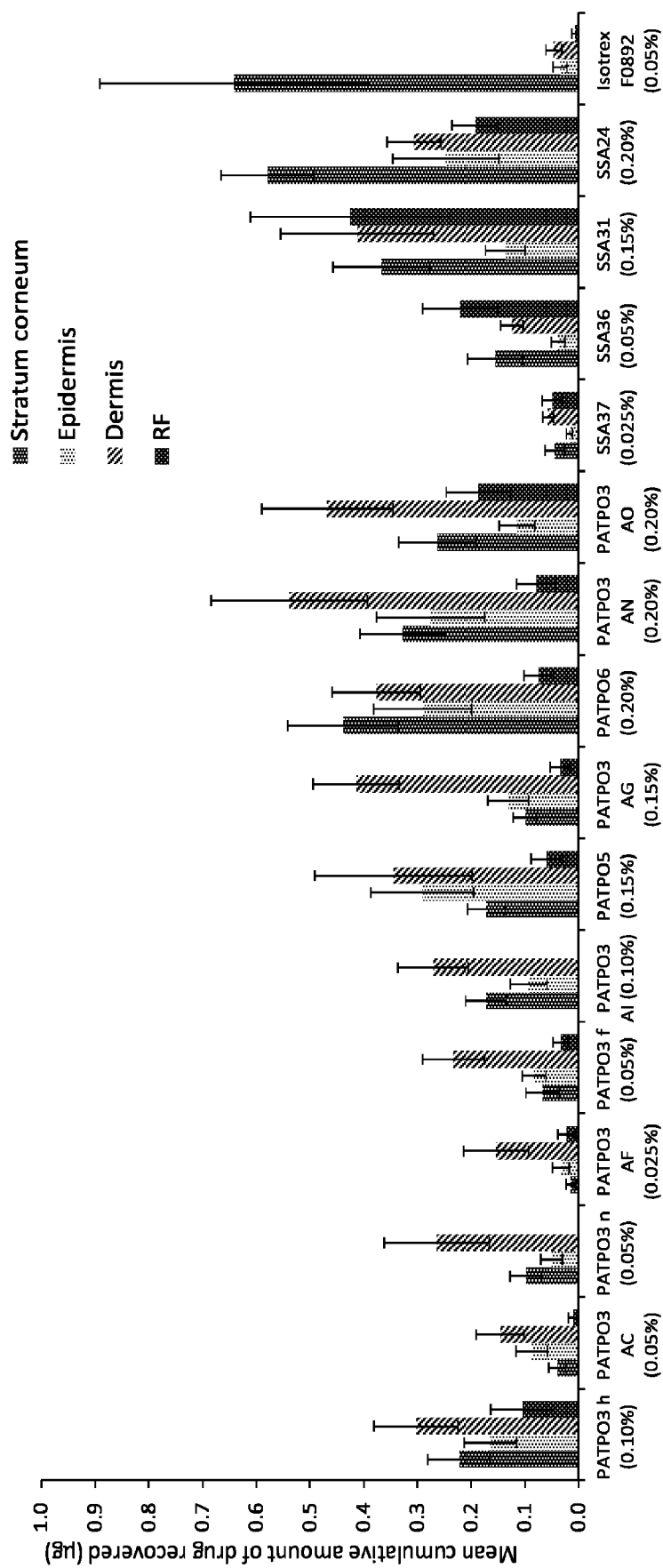
FIG. 10 is a bar graph highlighting the recovery of isotretinoin (µg) from the skin strata (*Stratum corneum*, epidermis, dermis) and receiver fluid following the application of certain tested formulations and comparator product, Isotrex gel 0.05%, after the final sampling point (48 h) (mean±SE, 10≤n≤12). SC denotes *Stratum corneum*.
Figure 13:
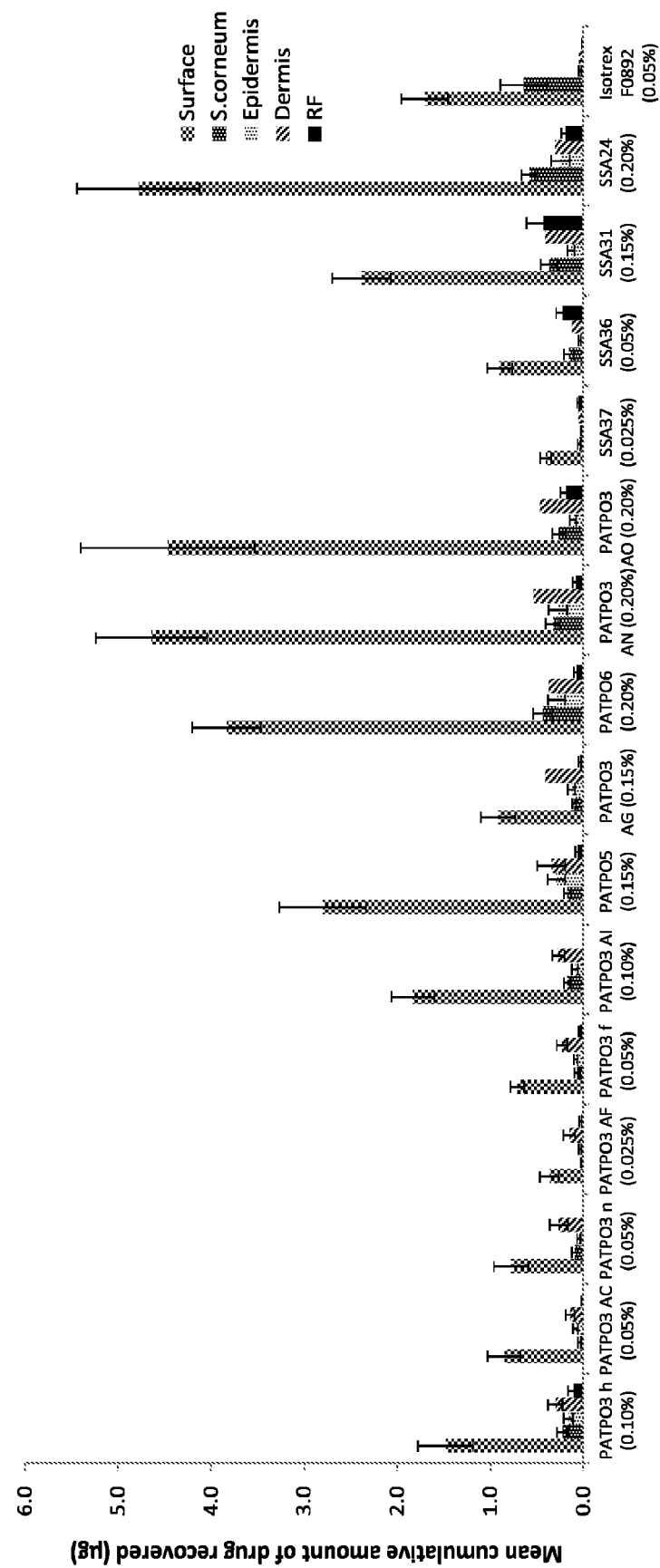
FIG. 13 is a bar graph showing recovery of isotretinoin (µg) from the surface (residual formulation), skin strata (*Stratum corneum*, epidermis, dermis) and receiver fluid following the application of certain tested formulations and comparator product, Isotrex gel 0.05%, after the final sampling point (48 h) (mean±SE, 10≤n≤12). SC denotes *Stratum corneum*.

A total of 15 formulations were selected in addition to the comparator product (Isotrex gel 0.05%) for permeation and penetration analysis. FIG. 9 shows the amount of drug permeated across the skin into the receiver fluid at 6, 24 and 48 h, following application of all the formulations to the surface of the skin at T=0 h. FIG. 13 depicts the penetration profiles of the drug (using human skin from three donors) from all the prototype formulations investigated, at each of the five concentrations of isotretinoin, compared to that from Isotrex gel 0.05% (batch F0892). FIG. 10 highlights the amount of isotretinoin penetrated into the skin layers and receiver fluid, with the exclusion of the amount of drug recovered from the surface of the skin (residual formulation). The analysis of the permeation data showed that the amount of drug recovered in the receiver fluid was below the LOQ for most of the formulations tested, at 6 and 24 h. Exclusions to this trend were observed when the drug was formulated as PATPO3 AF 0.025%, PATPO3 h 0.10%, PATPO5 0.15%, PATPO3 AG 0.15%, PATPO3 AO 0.20%, SSA36 0.05%, SSA31 0.15% and SSA24 0.20%, where isotretinoin was detected in the receiver fluid (FIG. 9) at levels above the LOQ. The drug was recovered in the receiver fluid at 48 h, following the application of all the formulations, with the exception of PATPO3 N 0.05%, PATPO3 AI 0.10%.

The analysis of the penetration data showed that as a general trend the highest amount of isotretinoin was recovered from the surface of the skin after the application of all the tested formulations, with the highest amount of isotretinoin recovered being 4.78±0.66 µg (SSA24, 0.20%). The highest delivery of isotretinoin into the epidermal layer (site of action of the drug) was observed with the application of PATPO5 0.15% (0.29±0.10 µg), PATPO6 0.20% (0.29±0.09 µg) and PATPO3 AN 0.20% (0.28±0.10 µg), which provided levels of isotretinoin approximately 10-fold and significantly ($p \leq 0.05$) higher compared to those observed with Isotrex gel, 0.05% (0.03±0.01 µg).

The analysis of the data related to the amount of isotretinoin recovered from the dermis indicate that the formulations providing the highest levels of the drug into this skin layer were PATPO3 AN 0.20% (0.54±0.15 µg) and PATPO3 AO 0.20% (0.47±0.12 µg), which again were found to be ca. 10-fold and significantly higher ($p \leq 0.05$) compared to those achieved with Isotrex gel, 0.05% (0.05±0.01 µg). The highest level of isotretinoin recovered from the *Stratum corneum* was observed after the application of the comparator product Isotrex gel (0.64±0.25 µg), followed by SSA24 (0.58±0.09 µg) and PATPO6 0.20% (0.44±0.10 µg).

Figure 3:
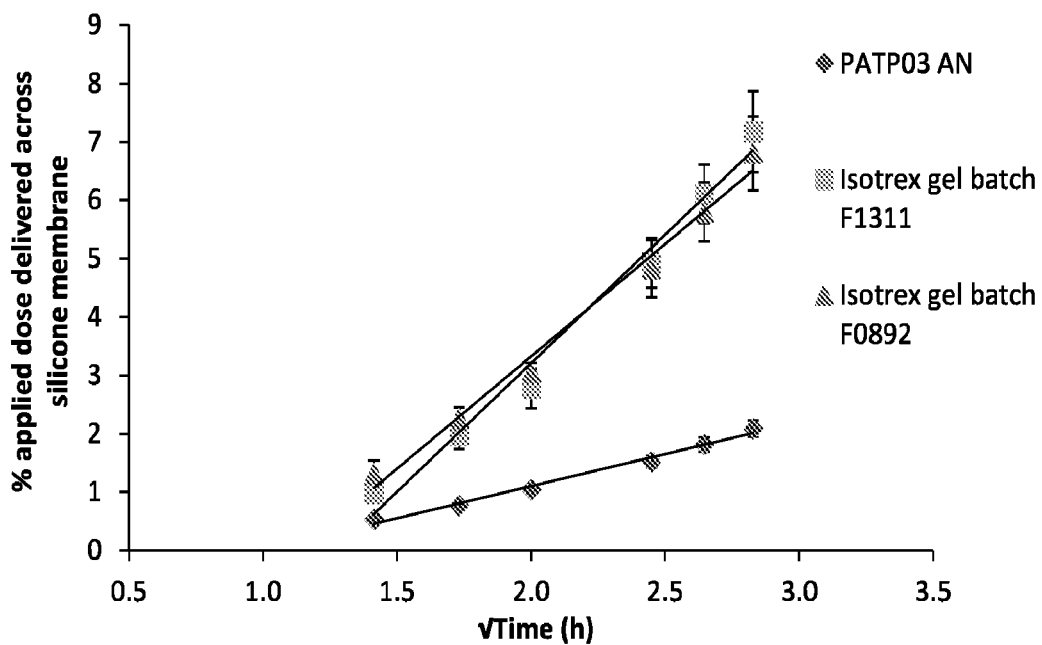
FIG. 3 is a line graph showing the percentage of applied dose of isotretinoin delivered from PATPO3 AN and comparator product, Isotrex gel 0.05% (batches: F1311 and F0892), through silicone membrane between 2 and 8 h (time represented as √time, mean±SE, 5≤n≤6).
Figure 4:
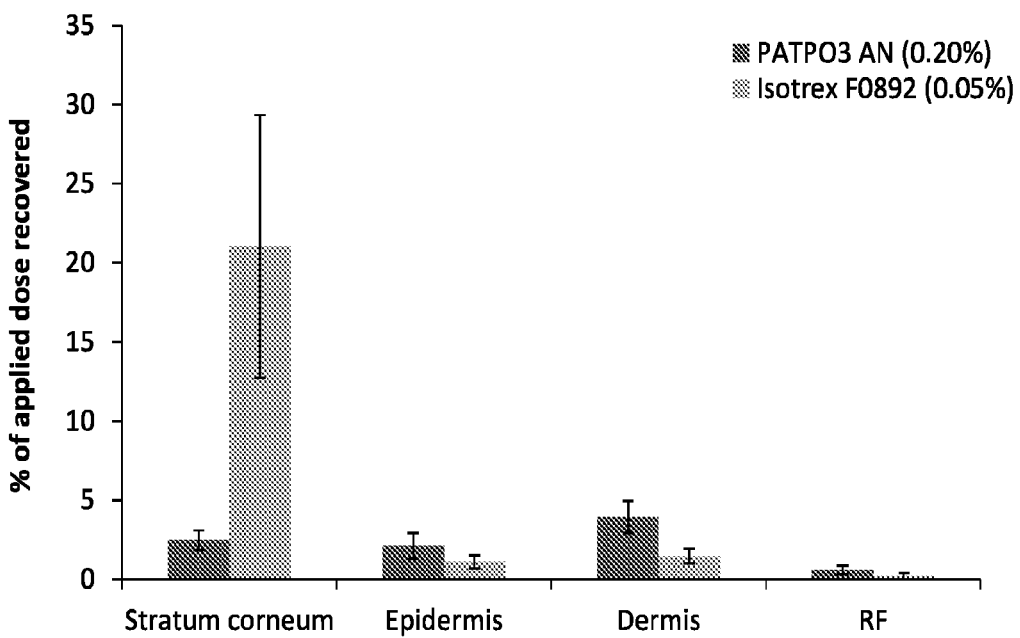
FIG. 4 is a bar graph showing the percentage of applied dose of isotretinoin recovered from skin strata (*Stratum corneum*, epidermis, dermis) and receiver fluid following the application of PATPO3 AN and comparator product, Isotrex gel 0.05% (batch F0892), after the final sampling point (48 h) (mean±SE, n=12).

Interestingly, as noted in EXAMPLE 1, the difference in the transport of isotretinoin across silicone from PATPO3 AN and Isotrex gel (FIG. 3) did not manifest into a similar relationship for delivery to the skin as shown in FIG. 4, where a 2-3 fold increase in the percentage of isotretinoin penetrated into the skin strata (epidermis and dermis) was observed following the application of PATPO3 AN (when expressed as % of applied dose). When the data was expressed as cumulative amount of drug permeated into and across the skin ($\mu g/cm^2$), the enhancement in the delivery of isotretinoin from PATPO3 AN to epidermal and dermal layers was measured to be approximately 10-fold, compared to Isotrex gel. The drug delivery profile of PATPO3 AN appears to be unique in that the delivery of drug appears to be targeted to the pathological site (epidermis/dermis) (despite the low levels of ethanol) unlike the Isotrex gel which has a more typical profile where delivery is focused to the *Stratum corneum* (FIG. 3). Thus, PATPO3 AN provides a unique targeted dermal delivery system that nevertheless resists systemic delivery.

Example 3

Stability Assessments

Following completion of the permeation/penetration experiment, accelerated stability testing on PATPO3 AN formulations containing 0.025% and 0.2% w/w isotretinoin, as set forth below in Table 5, where X=an isotretinoin assay and related substances, visual appearance, microscopic observations, and apparent pH; and A=backup.

TABLE 5

| Storage conditions | Initial t = 0 | 2 weeks | 4 weeks |
|---|---|---|---|
| 2-8° C. | X | A | X |
| 25° C. | | X | X |
| 40° C. | | X | X |

Figure 11A:
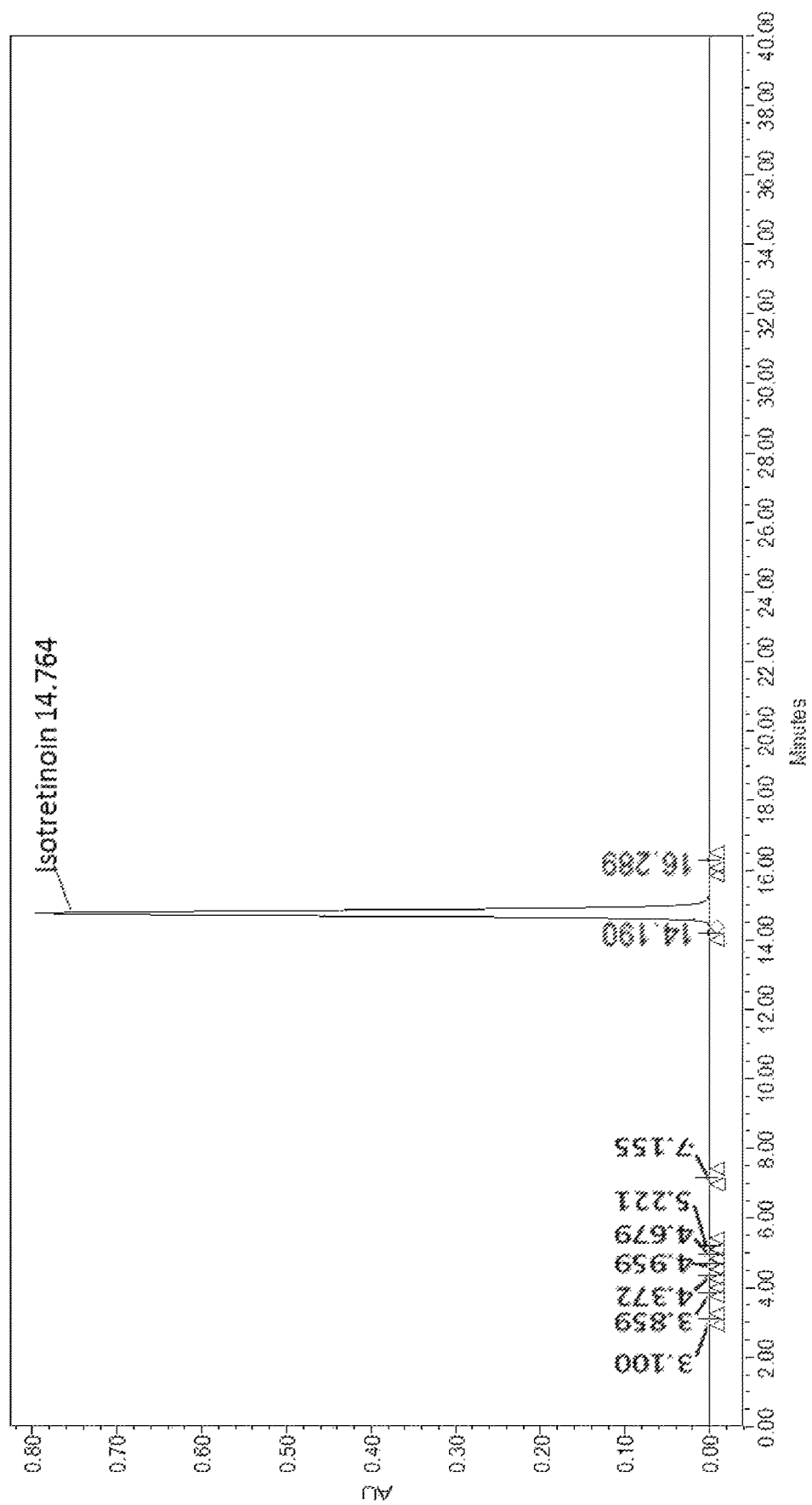
FIGS. 11A & 12B are chromatograms showing stability of the isotretinoin formulation PATPO3 AN containing 0.2% w/w isotretinoin, overlaid with PATPO3 AN placebo at t=0 weeks following storage at 40° C., between 2 and 17 minutes.
Figure 11B:
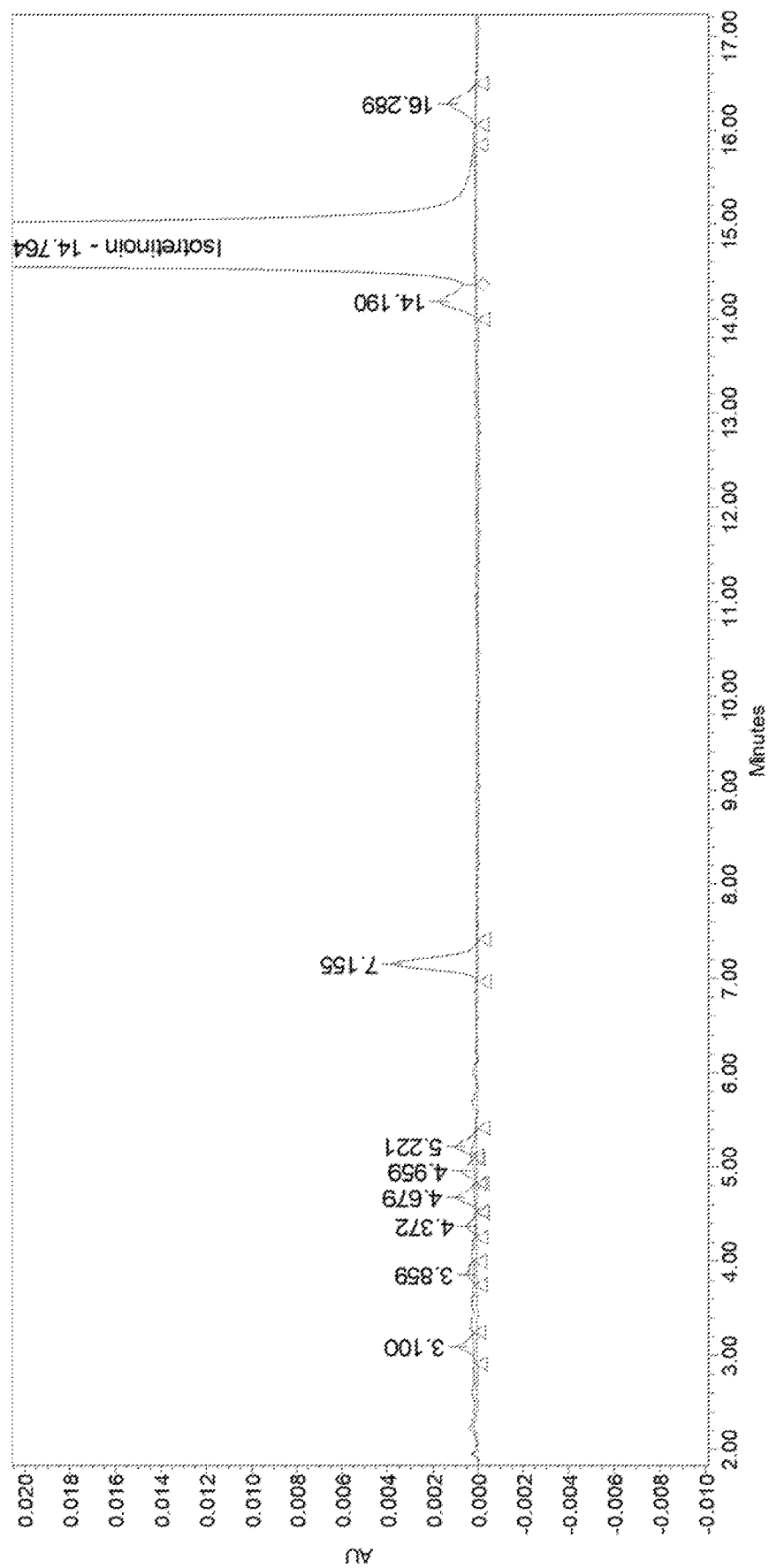
Figure 12B:
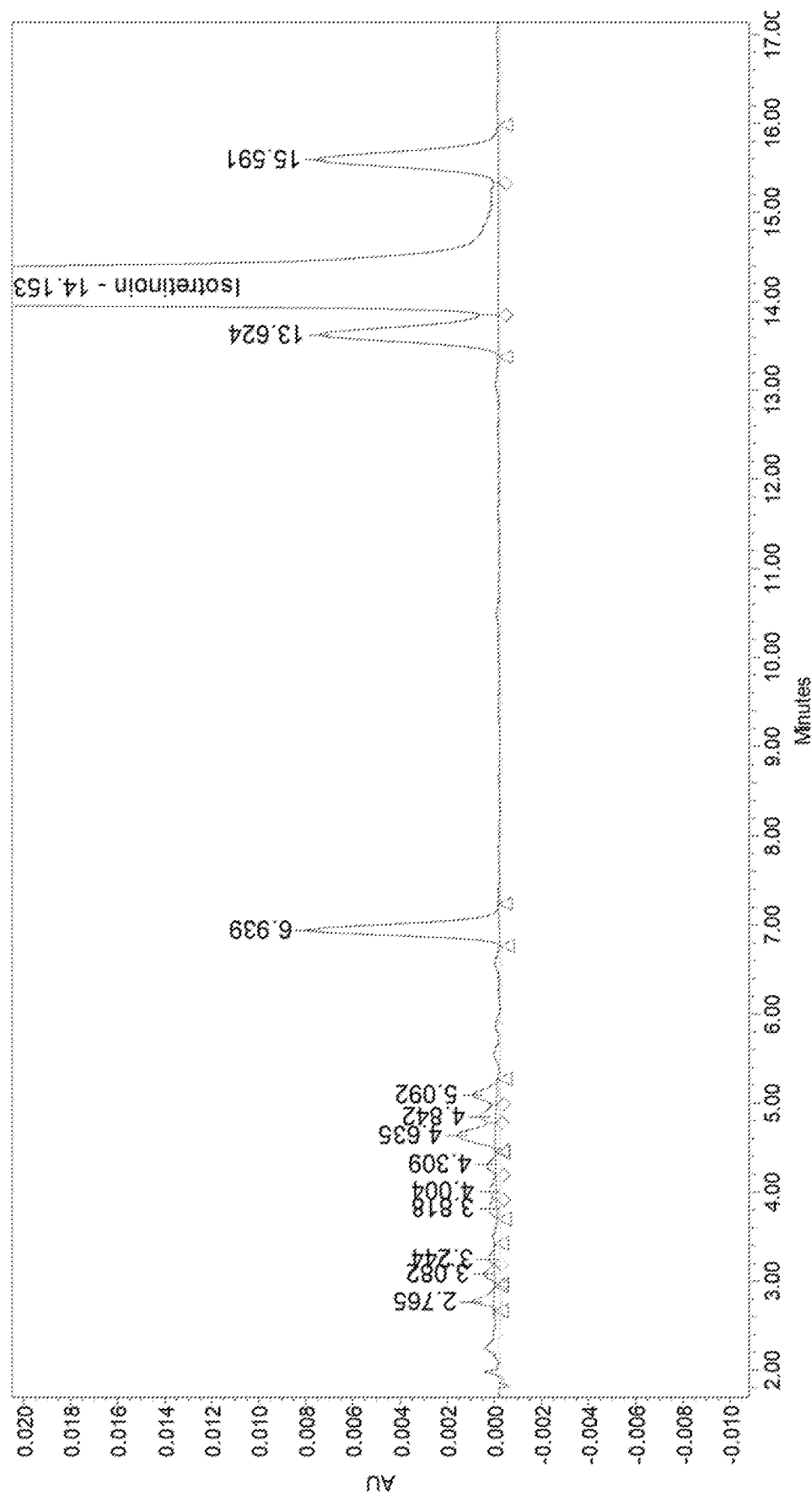

Representative batches of PATPO3 AN containing 0.2% w/w isotretinoin in sealed containers were stored at 2-8° C. (the stability of isotretinoin at this temperature was tested at 4 weeks only), 25° C. and 40° C. for four weeks and then tested using HPLC with n=3 replicates at t=2 and t=4 weeks. A PATPO3 AN placebo was tested for baseline comparison. The results are shown in FIGS. 11 and 12, which provide a representative chromatogram of PATPO3 AN containing 0.2% w/w isotretinoin, as compared against a placebo, between 2 and 17 minutes, at t=0 and t=4 weeks, respectively.

In addition, based on physical stability experiments (e.g., storage at 25° C. for up to 5 weeks after manufacture (with two freeze thaw cycles—between 2-8 and 25° C.) prior to assessment; centrifuge test ranging from 2-16 minutes of centrifuging), formulations with 0% to 2% w/w of ethanol show surprisingly improved physical stability (with reduced susceptibility to syneresis) during centrifuge tests relative to equivalent formulations with a higher ethanol content. Also, formulations with PEG 3350 shows improved physical stability (with reduced susceptibility to syneresis) relative to equivalent formulations prepared with PEG 4000.

Glycerol appears to improve physical stability where syneresis in formulations with propylene glycol occurs to a greater degree in 8% glycerol versus 15% glycerol formulations Here, only a very small droplet of liquid was observed, following centrifugation for 12-15 minutes, and could be distinguished from the main formulation by placement of glass pipette at the surface of the formulation.

Example 4

In Vivo Assessment

To evaluate the toxicity of the formulations herein, three concentrations of PATPO3 AN were administered daily as a topical ointment to miniature swine (*Sus scrofa*) for 90-days, followed by a 28-day recovery period. In addition, the toxicokinetic ("TK") characteristics of PATPO3 AN were evaluated.

Forty-eight (48) Hanford miniature swine were assigned to 5 groups, with 4 animals per gender per group in the main cohort and two additional animals per gender per group in the vehicle and high dose groups for the recovery cohort. Groups 1 through 5 were the sham, vehicle, low (0.1 mg/kg), mid (0.2 mg/kg) and high (0.4 mg/kg) dose groups, respectively. The dose of 0.2 g/kg was applied to a single site for each animal and was adequate to uniformly cover the entire 10% body surface area with a thin layer of PATPO3 AN. The size of the site (approximately 10% of the total body surface area for each animal) was based on the following formula:

$$10\% \text{ Total body surface area (cm}^2\text{)}=9.533 \text{ [BW (grams)]}^{2/3} \times 0.10$$

The average body surface area for each gender was used to determine the approximate 10% body surface for each study animal. Dose sites were clipped with electric clippers (blade no. 40 or finer) between Day −3 and Day −1, and at least the corners of the dose sites were marked with a permanent marker. Dose sites were re-clipped and re-marked throughout the study period as necessary. The size of the dose sites were adjusted throughout the study as needed. Prior to each dose administration, the dose site was washed with water soaked gauze and then dried with dry gauze. Prior to dose administration each day, tubes containing test article and vehicle used on that day were shaken at least 5 times. Animals were dosed (by weight) with the appropriate vehicle or test article daily, which remained in place for 24 hours±2 hours.

Animals were topically treated once per day for 90 days, followed by a 28-day recovery period. At designated time points, blood samples were collected for toxicokinetic ("TK") analysis. On Day 91, the main cohort animals were necropsied with tissue collection, followed by recovery cohort animals on Day 118.

Animals were evaluated for signs of toxicity through physical examinations, clinical observations, body weight, body weight change, dose site Draize scoring, clinical pathology (hematology, coagulation, serum chemistry and urinalysis), electrocardiography, ophthalmology, gross pathology, organ weight and histopathology. Toxicokinetic characteristics were assessed on study Day 1 and Day 90.

The study design, parameters evaluated, and TK sample collection scheme are presented in Tables 6, 7 and 8, respectively.

TABLE 6

Study Design

| Treatment Group | Test Article | Number of Animals Main Male | Number of Animals Main Female | Number of Animals Recovery Male | Number of Animals Recovery Female | Application Rate g/kg (mL/kg [a]) | Isotretinoin Conc. mg/g (%) | Isotretinoin Dose Level (mg/kg) |
|---|---|---|---|---|---|---|---|---|
| 1 (Sham) | N/A | 4 | 4 | N/A | N/A | N/A | N/A | N/A |
| 2 (Vehicle) | Vehicle | 4 | 4 | 2 | 2 | 0.2 (0.19) | N/A | 0 |
| 3 (Low) | PATP03 AN | 4 | 4 | N/A | N/A | 0.2 (0.19) | 0.5 (0.05%) | 0.1 |
| 4 (Mid) | | 4 | 4 | N/A | N/A | 0.2 (0.19) | 1.0 (0.1%) | 0.2 |
| 5 (High) | | 4 | 4 | 2 | 2 | 0.2 (0.19) | 2.0 (0.2%) | 0.4 |

Study Day 1 corresponds to the first day of dose administration.
[a] Formulation density = 1.068 g/mL

TABLE 7

Parameters Evaluated and Intervals

| Parameters | Approximate Intervals |
|---|---|
| Mortality/Moribundity observations | At least twice daily |
| Physical examination | During acclimation |
| Clinical observations | Once during acclimation<br>Prior to each dose on Days 1-90<br>Then daily thereafter on Days 91-118 |
| Draize score (dose site) | Once during acclimation<br>Prior to each dose on Days 1-7<br>Then weekly thereafter |
| Body weights | Prior to randomization, prior to first dose, weekly thereafter and prior to termination |
| Ophthalmology | During acclimation (main & recovery), prior to termination of main cohort (main & recovery), and prior to termination of recovery cohort |
| Clinical Pathology (hematology, serum chemistry, coagulation, & urinalysis) | During acclimation (main & recovery), prior to termination of main cohort (main & recovery), and prior to termination of recovery cohort |
| ECG | During acclimation (main & recovery), prior to termination of main cohort (main & recovery), and prior to termination of recovery cohort |
| Toxicokinetics | Day 1 and 90 |
| Necropsy/organ weights | Day 91 main animals and Day 118 recovery animals |
| Histopathology | Dose site and control skin on all animals (main and recovery), standard tissues on all study animals (main & recovery) in all groups, including gross lesions (if any) |

TABLE 8

TK Blood Collection Scheme

| Study Day | Target Sample Collection Time Points |
|---|---|
| 1 (Groups 1-5) | Pre, 0.5, 1, 2, 4, 6, 8, 12, 16, and 24 hours postdose |
| 90 (Groups 1-5) | Pre, 0.5, 1, 2, 4, 6, 8, 12, 16, and 24 hours postdose |

Blood samples were collected into tubes containing $K_2$-EDTA as the anticoagulant. Plasma samples were prepared by centrifuging at ~3000 rpm for approximately 15 minutes at ~4° C. All of the plasma samples were aliquoted in a single container and frozen on dry ice. The plasma samples were stored in a freezer at approximately −70° C. until shipment on dry ice to the analytical lab for analysis. All samples from all animals were collected according to Table 8 on Days 1 and 90. Groups 1 and 2 only had the 2-hour post-dose sample analyzed for isotretinoin and tretinoin for Days 1 and 90. Groups 3-5 had all samples analyzed for isotretinoin and tretinoin for Days 1 and 90.

Animals, housing and environmental conditions used for this assessment is found in Table 9.

TABLE 9

Animals, Housing and Environmental Conditions

| Species: | *Sus scrofa*, miniature swine |
|---|---|
| Strain: | Hanford, naïve |
| Source: | Sinclair Bio-Resources, LLC |
| Age at Acclimation: | 2.5-4.0 months |
| Weight at Week-1: | 9.5-17.3 kg |
| Number and Gender: | 48 (24 males and 24 females) |
| Identification: | Numbered ear tag and cage card |
| Acclimation: | At least 14 days |
| Caging: | Animals were housed in ~3' × 5' stainless steel solid lower walls with upper vertical bars and front gate and elevated PVC-coated expanded metal flooring |
| Enrichment | A steel chain suspended by a rope was provided in each pen for animals as enrichment |
| Number per cage: | 1 |
| Environmental conditions: | Temperature: 20.3° C. to 26.4° C. (68.5° F. to 79.5° F.) |
| Photoperiod: | 12-hr light/12-hr dark |

Detailed clinical observations were made once during acclimation, prior to dosing on Days 1-90, and then daily thereafter from Days 91-118. The dose sites were observed and scored for skin irritation once during acclimation, prior to each dose on Days 1-7, and then weekly thereafter until study termination. Local findings at the dose sites were scored using a modified Draize-scoring system (Table 10) to determine the degree of inflammation (erythema and edema).

TABLE 10

Draize Scoring System

| Category | Score | Description |
|---|---|---|
| Erythema | 0 | No erythema |
| | 1 | Slight erythema |
| | 2 | Well-defined erythema |

TABLE 10-continued

Draize Scoring System

| Category | Score | Description |
|---|---|---|
| | 3 | Moderate or severe erythema |
| | 4 | Severe erythema or slight eschar formation (injuries in depth) |
| Edema | 0 | No edema |
| | 1 | Very slight edema |
| | 2 | Slight edema (well-defined edges) |
| | 3 | Moderate edema (raised >1 mm) |
| | 4 | Severe edema (raised >1 mm and extending beyond the area of exposure) |

Ophthalmology examinations were performed during acclimation (main and recovery cohorts), prior to main cohort termination, and prior to termination of recovery cohort. A board-certified veterinary ophthalmologist performed all ocular examinations. The examinations included, but were not limited to, the conjunctiva, cornea, anterior chamber, iris, lens, vitreous humor, retina, and ocular fundus. An appropriate mydriatic agent was administered prior to the examination.

Electrocardiography (ECG) were performed on all study animals during acclimation (main and recovery cohorts), prior to main cohort termination, and prior to recovery cohort termination. The animals' hair at the sites to which the electrodes were attached was clipped and moistened with gel before placement. The appropriate electrodes were attached according to the electrocardiogram machine manufacturer's instructions with settings consistent with conventional veterinary procedures. Recordings of the standard leads I, II, and III were collected at paper speeds of 25 mm/sec and 50 mm/sec with a minimum of three complexes for each recording. ECG recording times were for 20 to 60 seconds at 25 mm/sec to assess arrhythmias and a brief tracing at 50 mm/sec for ease of measurement of P-QRS-T waveforms The ECG data was submitted to a board-certified veterinary cardiologist for interpretation of qualitative parameters (i.e., abnormalities in rhythm, conduction, etc.) and quantitative data, including, but not limited to: HR, RR, PR, QRS, QT and QTc intervals.

For clinical pathology, blood samples were collected from study animals for clinical pathology tests during acclimation (main and recovery cohorts), prior to main cohort termination (main and recovery cohorts), and prior to recovery cohort termination.

Blood samples (~2 mL/animal) were collected into a tube containing $K_3$-EDTA as anticoagulant. Samples were stored on wet ice or refrigerated at ~4° C. until analyzed. The hematology analysis included:

| | |
|---|---|
| White blood cell count | Neutrophils (% and absolute) |
| Red blood cell count | Eosinophils (% and absolute) |
| Hemoglobin | Basophils (% and absolute) |
| Hematocrit | Lymphocytes (% and absolute) |
| Mean cell volume | Monocytes (% and absolute) |
| Mean cell hemoglobin | Platelet count |
| Mean cell hemoglobin concentration | Reticulocytes |
| Differential white blood cell count | |

Blood samples (~1.8 mL/animal) were collected into tubes containing sodium citrate (3.2%). Plasma was prepared by centrifuging for ~15 minutes at ~3000 rpm at ~4° C. Plasma was stored temporarily on wet ice or refrigerated at 4° C. until analyzed. The coagulation analysis included:

| | |
|---|---|
| Activated partial thromboplastin time (APTT) | Prothrombin time (PT) |
| Fibrinogen | |

With respect to serum chemistry Blood samples (~2 mL/animal) were collected from each animal, into tubes without anticoagulant. Blood was allowed to clot before being centrifuged for ~15 minutes at ~3000 rpm at ~4° C. and serum was harvested into a polypropylene cryovial. Serum was stored temporarily on wet ice or refrigerated at 4° C. until analyzed. The serum chemistry analysis included:

| | |
|---|---|
| Alanine aminotransferase (ALT) | Creatinine |
| Albumin | Globulin |
| Albumin/Globulin ratio | Glucose |
| Alkaline phosphatase (ALP) | Inorganic phosphorus |
| Aspartate aminotransferase (AST) | Potassium |
| Blood Urea Nitrogen (BUN) | Sodium |
| Calcium | Total bilirubin |
| Chloride | Total protein |
| Cholesterol | Triglycerides |

Urine (~2 mL if available) was collected using metabolism cages overnight at room temperature. The sample was placed in a sterile red top tube without anticoagulant and stored on wet ice or refrigerated at ~4° C. until analyzed. The samples were analyzed for the following parameters:

| | |
|---|---|
| Bilirubin | Protein |
| Blood | Specific gravity |
| Color and clarity | Urobilinogen |
| Glucose | Urine microscopic examination including the |
| Ketones | presence of WBC, RBC, crystals and bacteria |
| pH | |

At scheduled sacrifices, the following organs (when present) were weighed, with paired organs weighed together. Relative organ weights (organ-to-body weight and organ-to-brain weight) ratios were calculated:

| | |
|---|---|
| adrenal (2) | pituitary gland |
| Brain | spleen |
| epididymis (2) | testis (2) |
| Heart | thymus |
| kidney (2) | thyroid |
| liver with gall bladder (drained) | uterus |

The following tissues (when present) from all animals were preserved in 10% neutral-buffered formalin (except where noted):

| | |
|---|---|
| adrenal (2) | ovary (2) with oviduct |
| aorta | pancreas |
| bone (femur & sternum with marrow) | pituitary gland |

-continued

| | |
|---|---|
| bone marrow smear*** | rectum |
| brain (cerebellum, cerebrum, medulla & pons) | salivary gland [mandibular (2)] |
| cecum | sciatic nerve |
| cervix | seminal vesicle (2) |
| colon | skeletal muscle (quadriceps femoris) |
| duodenum | skin—abdomen |
| epididymis (2) | skin—from dose site with underlying tissue |
| esophagus | skin—from non-dose site with underlying tissue |
| eyes (2) with optic nerve* | spinal cord (cervical, thoracic & lumbar) |
| heart | spleen |
| ileum | stomach |
| jejunum | testis (2)* |
| kidney (2) | thymus |
| Lacrimal gland | thyroid (2) |
| lesions** | tongue |
| liver with gallbladder (drained) | trachea |
| lung with main stem bronchi | urinary bladder |
| lymph nodes (mandibular) | uterus |
| lymph node (mesenteric) | vagina |
| mammary gland (females) | |

*Eyes and testes were fixed in Davidson's and Modified Davidson's, respectively for 1-3 days and then both were stored in 70% alcohol.
**Gross lesions were collected.
***Bone marrow smears were fixed in methanol and retained for evaluation at the discretion of the Study Director in consultation with the study pathologist and Sponsor.

All preserved tissues were submitted to Histo-Scientific Research Laboratories ("HSRL"). Main and Recovery cohort animals had preserved tissues embedded in paraffin, sectioned, stained with hematoxylin and eosin, and examined microscopically by a board-certified veterinary pathologist. Gross lesions were examined microscopically. Following histopathology evaluations, all prepared slides, remaining wet tissues, blocks, and raw data were returned for archive.

Once daily topical (dermal) application of PATP03 AN to 10% of the total body surface of miniature swine for 90 days at up to 0.4 mg/kg/day resulted in no toxicologically meaningful effects on mortality/moribundity, non-dermal clinical observations, body weight gain, ophthalmologic or electrocardiographic examinations, hematology, serum chemistry or urinalysis parameters, or organ weights. There were no unscheduled deaths or significant moribundity for any animal. Dermal effects observed were consistent with the well-known characteristics of topically applied retinoids.

Analysis of plasma isotretinoin/tretinoin parameters showed minimal isotretinoin systemic exposure following a single PATP03 AN application with tretinoin exposure greater than that of isotretinoin. With repeat PATP03 AN dermal administration, isotretinoin exposure plateaued at the mid-dose level (0.2 mg/kg). Isotretinoin accumulation was evident, but without an associated increase in tretinoin exposure. A systemic No Observable Adverse Effect Level ("NOAEL") of 0.4 mg/kg/day was identified (associated with a Day 90 isotretinoin AUC values of 44.3 hr*ng·mL).

Example 5

Additional Formulations

Table 11 lists four formulations at 0.2% w/w of isotretinoin and two formulations at 0.6% w/w of isotretinoin were assessed herein and compared against results of the comparator product, Isotrex gel 0.05%. Unlike Isotrex gel that has over 95% ethanol, the six formulations had no or much lower concentration (e.g., 2%) of ethanol, respectively. Additionally, five of the six formulations (EtOH 2%/PEG3350; PATPO3 PEG only with 1450-b; PATPO3 f-d, 5% glycerol, PEG3350; EtOH 2%/PEG3350; and PATPO3 PEG only with 1450-b) did not include water.

TABLE 11

| | Target composition % w/w | | | | | |
|---|---|---|---|---|---|---|
| Excipient | EtOH 2%/ PEG3350 (0.2% API) | Water 5%/ PEG3350 (0.2% API) | PATPO3 PEG only with 1450-b (0.2% API) | PATPO3 f-d, 5% Glycerol, PEG3350 (0.2% API) | EtOH 2%/ PEG3350 (0.6% API) | PATPO3 PEG only with 1450-b (0.6% API) |
| SR PEG 400 | 67.58 | 65.38 | 69.3 | 69.7 | 67.18 | 69.3 |
| Water | — | 5 | — | — | — | — |
| Glycerol | — | — | — | 5 | — | — |
| Ethanol | 2 | — | — | — | 2 | — |
| Methyl parabens | 0.2 | 0.2 | 0.2 | 0.2 | 0.2 | 0.2 |
| Propyl parabens | 0.02 | 0.02 | 0.02 | 0.02 | 0.02 | 0.02 |
| PEG 4000 | — | — | — | — | — | — |
| PEG 3350 | 29.9 | 29.1 | 14.78 | 14.78 | 29.9 | 14.78 |
| PEG-1450 | — | — | 15 | 10 | — | 15 |

TABLE 11-continued

| Excipient | EtOH 2%/ PEG3350 (0.2% API) | Water 5%/ PEG3350 (0.2% API) | PATPO3 PEG only with 1450-b (0.2% API) | PATPO3 f-d, 5% Glycerol, PEG3350 (0.2% API) | EtOH 2%/ PEG3350 (0.6% API) | PATPO3 PEG only with 1450-b (0.6% API) |
|---|---|---|---|---|---|---|
| BHT | 0.1 | 0.1 | 0.1 | 0.1 | 0.1 | 0.1 |
| Isotretinoin | 0.2 | 0.2 | 0.2 | 0.2 | 0.6 | 0.6 |
| Total | 100 | 100 | 100 | 100 | 100 | 100 |

(—): not included.

Figure 14:
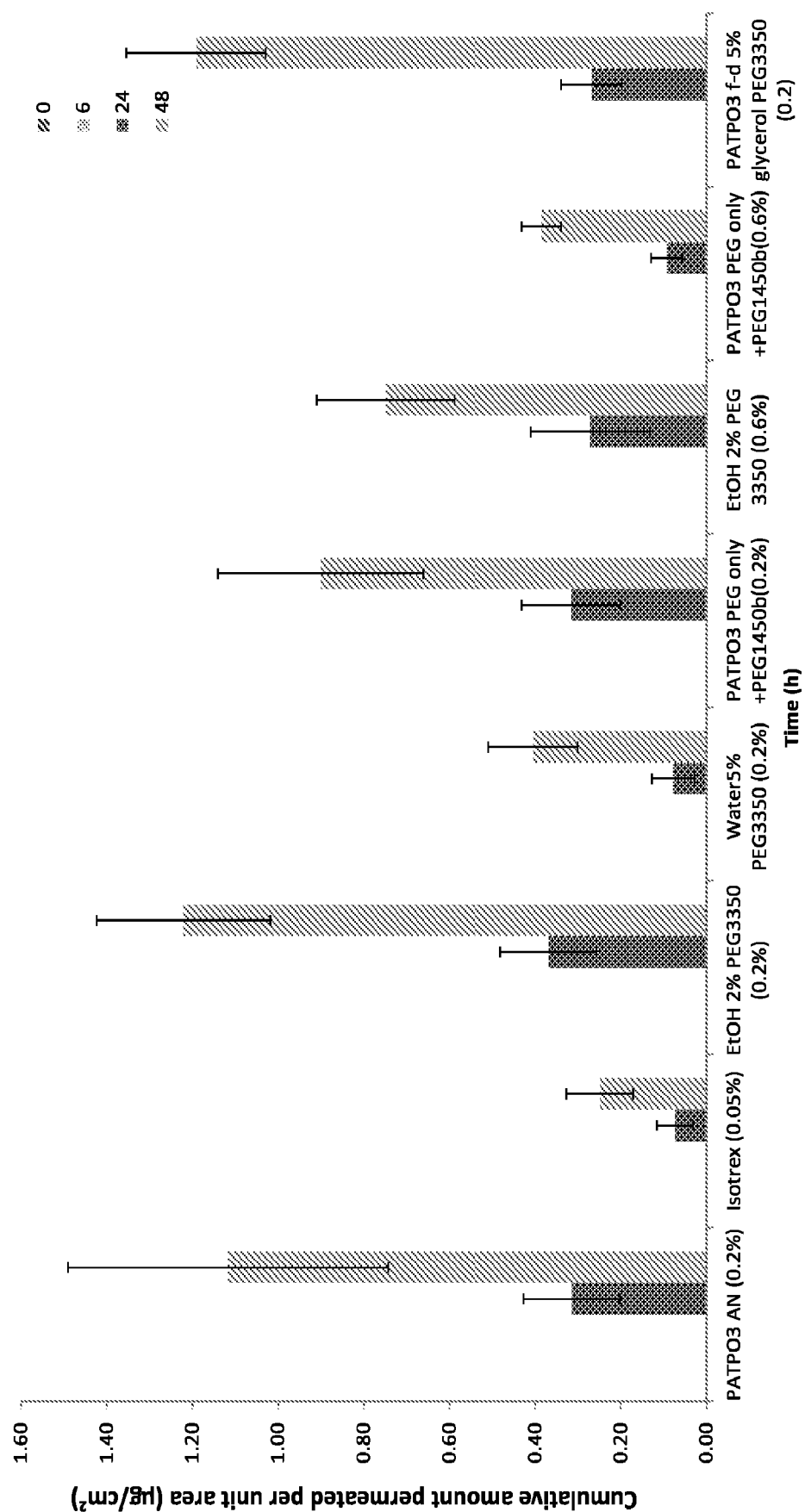
FIG. 14 is a bar graph showing the cumulative amount of isotretinoin permeated across the skin (µg/cm²) into the receiver fluid following the application of certain tested formulations and comparator product, Isotrex gel 0.05%, after final sampling point (24 h) (mean±SE, 10≤n≤12).
Figure 15:
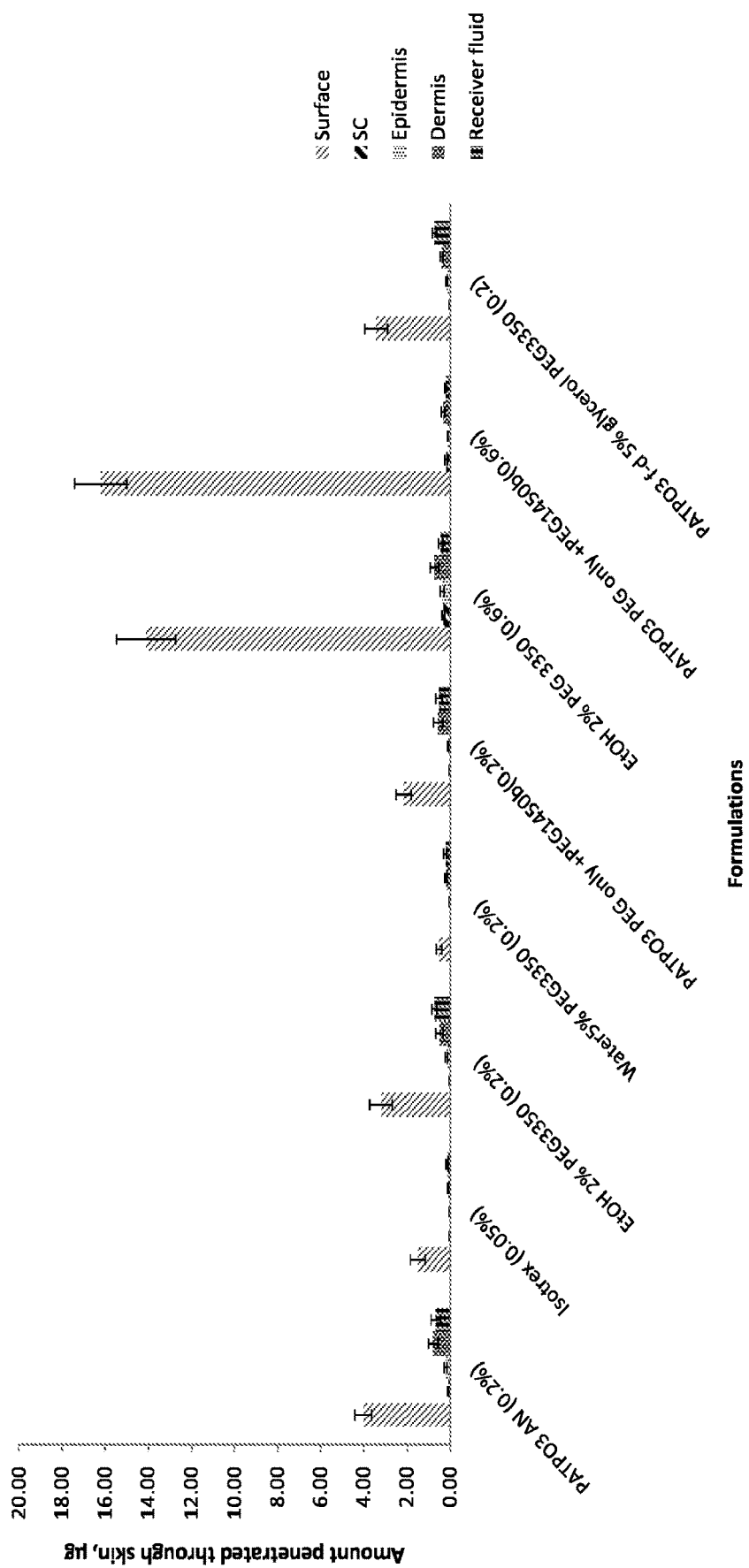
FIG. 15 is a bar graph showing the amount of isotretinoin penetrated through the skin (µg) from the surface (residual formulation), skin strata (*Stratum corneum*, epidermis, dermis) and receiver fluid following the application of certain tested formulations and comparator product, Isotrex gel 0.05%, after the final sampling point (48 h) (mean±SE, 10≤n≤12). SC denotes *Stratum corneum*.
Figure 17:
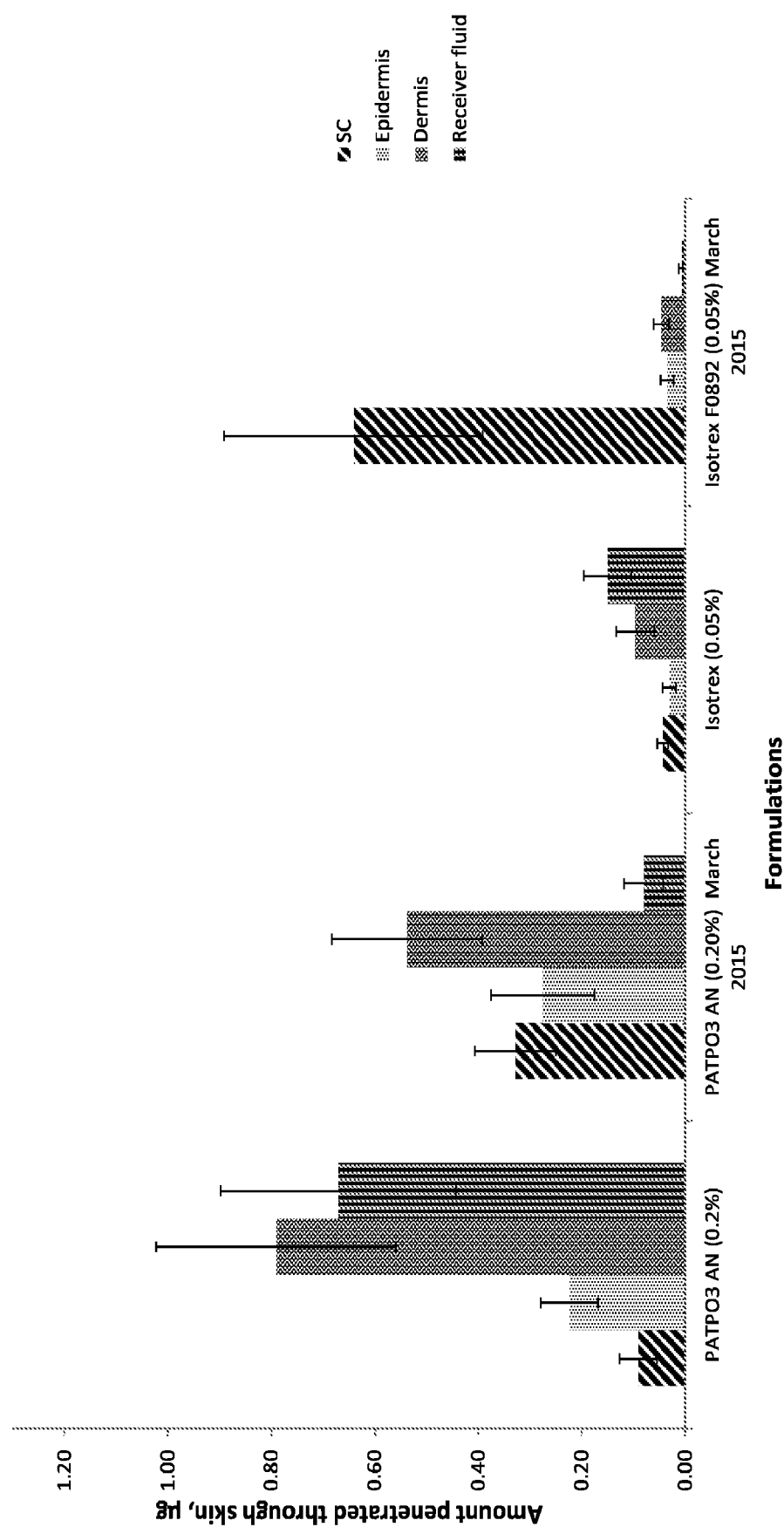
FIG. 17 is a bar graph showing, the amount of isotretinoin penetrated through the skin (µg) from skin strata (*Stratum corneum*, epidermis, dermis) and receiver fluid following the application of all PATPO3 AN (0.2%) (first and second data sets from the left) and Isotrex gel 0.05% (third and fourth data sets from the left), respectively, after the final sampling point (48 h) (mean±SE, 10≤n≤12). SC denotes *Stratum corneum*. The first (PATPO3 AN) and third (Isotrex (0.05%)) data sets from the left are based on a fourth skin donor, while the second (PATPO3 AN) and fourth (Isotrex F0892 (0.05%)) data sets are based on first three skin donors.

FIGS. 14 and 15 show results using the six formulations listed in Table 11 against the comparator product, Isotrex gel 0.05% using the same in vitro skin permeation and penetration experiment parameters, procedures and data calculations discussed in EXAMPLE 2 above. However, the dermatoned skin used for these experiments came from a fourth donor. As shown in FIG. 14, isotretinoin was not found in the receiver fluid for the t=0 and 6-hour time points for any of the formulations tested. However, after 24 hours, isotretinoin is found in the receiver fluid in minimal amounts in the tested formulations, including Isotrex and PATPO3 AN. These results show greater permeability when comparing the results in FIG. 9, which shows that isotretinoin in receiver fluid did not occur until 48 hours. This may be due to greater permeability from the fourth donor than the three donors used during the previous assessment discussed earlier. See also FIG. 17, which shows a comparison of two skin penetration data sets of PATPO3 AN (0.2%) and Isotrex (0.05%), respectively, and that the first and third data sets from the left, which both are based on the fourth donor, show greater permeability than the second and fourth data sets from the left, which both are based on the three previous donors.

Figure 16:
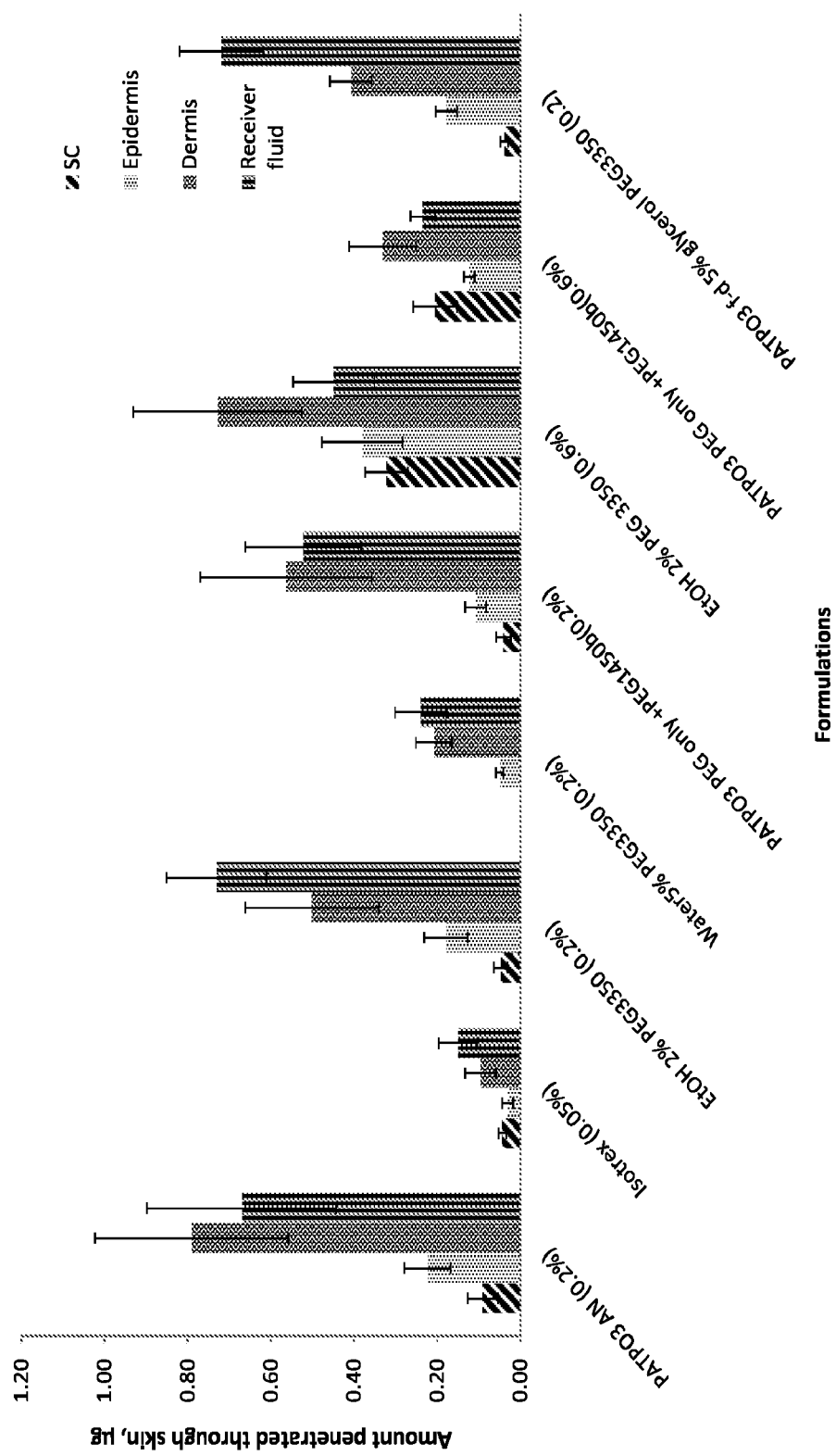
FIG. 16 is a bar graph showing, with the surface removed, the amount of isotretinoin penetrated through the skin (µg) from skin strata (*Stratum corneum*, epidermis, dermis) and receiver fluid following the application of certain tested formulations and comparator product, Isotrex gel 0.05%, after the final sampling point (48 h) (mean±SE, 10≤n≤12). SC denotes *Stratum corneum*.

FIG. 16 shows that the following formulations demonstrate unexpected, superior delivery of isotretinoin to the epidermis and dermis than Isotrex gel: PATPO3 AN; EtOH 2%/PEG3350; PATPO3 PEG only with 1450-b; and PATPO3 f-d, 5% glycerol, PEG3350. Again, these formulations have much a lower concentration of to no ethanol, which is in severe contrast to the more than 95% ethanol in Isotrex gel. Formulations prepared at 0.6% w/w do not appear to deliver more isotretinoin than formulations prepared at 0.2% w/w. Hence, the novel formulations disclosed herein show unexpected, superior delivery efficiency of isotretinoin to the epidermis and dermis, and that such delivery efficiency is not simply a result of increasing the amount of isotretinoin in the formulation. Indeed, FIG. 15 confirms that a large amount of isotretinoin remained at the skin surface for the 0.6% w/w isotretinoin formulations (see, e.g., FIG. 15: EtOH 2% PEG 3350 (0.6%) and PATPO3 PEG only +PEG1450b (0.6%)).

The various aspects of the invention described above can be combined to provide further aspects of the invention. All of the references and products referred to in this application are in their entirety incorporated herein by reference. Aspects of the invention can be modified, if necessary to employ concepts of the references and/or products referred to in this application.

In general, in the following claims, the terms used should not be construed to limit the claims to the specific aspects disclosed in the specification and the claims, but should be construed to include all possible aspects along with the full scope of equivalents to which such claims are entitled. Accordingly, the claims are limited by the disclosure.

What is claimed is:

1. A pharmaceutical composition consisting of PEG 400, PEG 3350, PEG 1450, butylated hydroxytoluene (BHT), methyl paraben, propyl paraben, and about 0.01% w/w to about 0.6% w/w isotretinoin, wherein the pharmaceutical composition has 0% w/w of ethanol and 0% w/w of water, and is formulated as a gel, ointment, lotion, emulsion, or cream.

2. The pharmaceutical composition of claim 1, wherein the pharmaceutical composition has about 69% to about 70% w/w PEG 400, about 15% w/w PEG 3350 and about 15% w/w PEG 1450.

3. The pharmaceutical composition of claim 2, wherein the pharmaceutical composition has about 0.2% w/w methyl paraben and about 0.02% w/w propyl paraben.

4. The pharmaceutical composition of claim 3, wherein the pharmaceutical composition has about 0.1% w/w BHT.

5. A pharmaceutical composition consisting of about 0.01% w/w to about 0.2% w/w isotretinoin, about 69% w/w to about 70% w/w PEG 400, about 15% w/w PEG 3350, about 15% w/w PEG 1450, about 0.1% w/w butylated hydroxytoluene (BHT), about 0.2% w/w methyl paraben, and about 0.02% w/w propyl paraben, wherein the pharmaceutical composition has 0% w/w of ethanol and 0% w/w of water, and is formulated as a gel, ointment, lotion, emulsion, or cream.

6. The pharmaceutical composition of claim 5, wherein the pharmaceutical composition has about 0.01% w/w, about 0.025% w/w, about 0.05% w/w, about 0.1% w/w, about 0.15% w/w, or about 0.2% w/w isotretinoin.

7. A pharmaceutical composition consisting of 0.01% w/w to 0.2% w/w isotretinoin, 69% w/w to 70% w/w PEG 400, 14.78% w/w PEG 3350, 15% w/w PEG 1450, 0.1% w/w butylated hydroxytoluene (BHT), 0.2% w/w methyl paraben, and 0.02% w/w propyl paraben, wherein the pharmaceutical composition has 0% w/w of ethanol and 0% w/w of water, and is formulated as a gel, ointment, lotion, emulsion, or cream.

8. The pharmaceutical composition of claim 7, wherein the pharmaceutical composition has 0.01% w/w, 0.025% w/w, 0.05% w/w, 0.1% w/w, 0.15% w/w, or 0.2% w/w isotretinoin.

9. A pharmaceutical composition consisting of PEG 400, PEG 3350, PEG 1450, butylated hydroxytoluene (BHT), methyl paraben, propyl paraben, and 0.01% w/w to 0.6% w/w isotretinoin, wherein the pharmaceutical composition has 0% w/w of ethanol and 0% w/w of water, and is formulated as a gel, ointment, lotion, emulsion, or cream.

10. The pharmaceutical composition of claim 9, wherein the pharmaceutical composition has 69% to 70% w/w PEG 400, 15% w/w PEG 3350 and 15% w/w PEG 1450.

11. The pharmaceutical composition of claim 10, wherein the pharmaceutical composition has 0.2% w/w methyl paraben and 0.02% w/w propyl paraben.

12. The pharmaceutical composition of claim 11, wherein the pharmaceutical composition has 0.1% w/w BHT.

* * * * *